(12) United States Patent
Sibbitt, Jr. et al.

(10) Patent No.: US 8,932,324 B2
(45) Date of Patent: Jan. 13, 2015

(54) REDUNDANT TISSUE CLOSURE METHODS AND APPARATUSES

(75) Inventors: Wilmer L. Sibbitt, Jr., Albuquerque, NM (US); Robert M. Curtis, Santa Fe, NM (US); Randy R. Sibbitt, Helena, MT (US)

(73) Assignee: Abbott Vascular Inc., Santa Clara, CA (US)

( * ) Notice: Subject to any disclaimer, the term of this patent is extended or adjusted under 35 U.S.C. 154(b) by 520 days.

(21) Appl. No.: 12/559,377

(22) Filed: Sep. 14, 2009

(65) Prior Publication Data

US 2010/0130965 A1     May 27, 2010

Related U.S. Application Data

(63) Continuation of application No. 12/365,397, filed on Feb. 4, 2009, now Pat. No. 8,048,108, which is a continuation of application No. 11/316,775, filed on Dec. 23, 2005, now abandoned, application No.

(Continued)

(51) Int. Cl.
*A61B 17/08*     (2006.01)
*A61D 1/00*     (2006.01)
*A61B 17/064*     (2006.01)
*A61B 17/00*     (2006.01)

(52) U.S. Cl.
CPC ... *A61B 17/0057* (2013.01); *A61B 2017/00663* (2013.01); *A61B 17/0643* (2013.01); *A61B 2017/00668* (2013.01); *A61B 2017/0641* (2013.01)
USPC ............................ 606/213; 606/148; 606/149

(58) Field of Classification Search
USPC ......... 606/113, 139, 144, 145, 148, 149, 151, 606/228, 213
See application file for complete search history.

(56) References Cited

U.S. PATENT DOCUMENTS

| | | | |
|---|---|---|---|
| 1,242,139 A | 10/1917 | Callahan |
| 1,480,935 A | 1/1924 | Gleason |
| 2,108,206 A | 2/1938 | Meeker |
| 2,371,978 A | 3/1945 | Perham |
| 2,610,631 A | 9/1952 | Calicchio |
| 3,348,595 A | 10/1967 | Stevens, Jr. |
| 3,357,070 A | 12/1967 | Sloan |
| 3,682,180 A | 8/1972 | McFarlane |

(Continued)

FOREIGN PATENT DOCUMENTS

| | | |
|---|---|---|
| FR | 2768324 | 3/1999 |
| JP | 2000014634 A | 1/2000 |

(Continued)

OTHER PUBLICATIONS

U.S. Appl. No. 60/711,279, filed Aug. 24, 2005, Sibbitt, Jr. et al.

(Continued)

*Primary Examiner* — Dianne Dornbusch
(74) *Attorney, Agent, or Firm* — Workman Nydegger; Randy Shen

(57) ABSTRACT

A tissue closure device including a tissue eversion apparatus, and a first and a second, redundant closure element that are placed on the external surface of a tissue puncture wound to enhance the efficacy of closure. The first closure element and the second closure element are left resident on the external surface of or in proximity to the tissue puncture wound in order to provide redundancy of closure.

24 Claims, 11 Drawing Sheets

Related U.S. Application Data

12/559,377, which is a continuation-in-part of application No. 11/508,656, filed on Aug. 23, 2006, now Pat. No. 8,758,397, and a continuation-in-part of application No. 11/316,775, application No. 12/559,377, which is a continuation-in-part of application No. 11/508,715, filed on Aug. 23, 2006, and a continuation-in-part of application No. 11/318,775, application No. 12/559,377, which is a continuation-in-part of application No. 11/508,662, filed on Aug. 23, 2006, and a continuation-in-part of application No. 11/316,775.

(60) Provisional application No. 60/711,279, filed on Aug. 24, 2005.

(56) References Cited

U.S. PATENT DOCUMENTS

| | | | | |
|---|---|---|---|---|
| 3,814,104 A | | 6/1974 | Irnich et al. | |
| 3,856,018 A | | 12/1974 | Perisse et al. | |
| 3,874,388 A | | 4/1975 | King et al. | |
| 3,908,662 A | | 9/1975 | Razgulov et al. | |
| 3,926,194 A | | 12/1975 | Greenberg et al. | |
| 3,939,820 A | | 2/1976 | Grayzel | |
| 3,985,138 A | | 10/1976 | Jarvik | |
| 4,011,872 A | | 3/1977 | Komiya | |
| 4,018,228 A | | 4/1977 | Goosen | |
| 4,018,229 A | * | 4/1977 | Komiya | 606/139 |
| 4,189,808 A | | 2/1980 | Brown | |
| 4,267,995 A | | 5/1981 | McMillan | |
| 4,501,276 A | | 2/1985 | Lombardi | |
| 4,697,312 A | | 10/1987 | Freyer | |
| 4,830,002 A | | 5/1989 | Semm | |
| 5,041,129 A | | 8/1991 | Hayhurst et al. | |
| 5,059,201 A | | 10/1991 | Asnis | |
| 5,100,422 A | | 3/1992 | Berguer et al. | |
| 5,176,691 A | | 1/1993 | Pierce | |
| 5,192,287 A | | 3/1993 | Fournier et al. | |
| 5,217,471 A | | 6/1993 | Burkhart | |
| 5,237,996 A | | 8/1993 | Waldman et al. | |
| 5,254,105 A | | 10/1993 | Haaga | |
| 5,290,284 A | * | 3/1994 | Adair | 606/37 |
| 5,300,078 A | | 4/1994 | Buelna | |
| 5,330,445 A | | 7/1994 | Haaga | |
| 5,336,231 A | * | 8/1994 | Adair | 606/148 |
| 5,354,279 A | | 10/1994 | Hofling | |
| 5,383,905 A | | 1/1995 | Golds et al. | |
| 5,403,330 A | | 4/1995 | Tuason | |
| 5,403,331 A | | 4/1995 | Chesterfield et al. | |
| 5,404,621 A | | 4/1995 | Heinke | |
| 5,425,740 A | | 6/1995 | Hutchinson, Jr. | |
| 5,462,561 A | | 10/1995 | Voda | |
| 5,466,241 A | | 11/1995 | Leroy et al. | |
| 5,478,353 A | * | 12/1995 | Yoon | 606/213 |
| 5,478,354 A | | 12/1995 | Tovey et al. | |
| 5,486,186 A | | 1/1996 | Yoon | |
| 5,489,288 A | | 2/1996 | Buelna | |
| 5,492,119 A | | 2/1996 | Abrams | |
| 5,507,744 A | | 4/1996 | Tay et al. | |
| 5,536,267 A | | 7/1996 | Edwards et al. | |
| 5,562,684 A | | 10/1996 | Kammerer | |
| 5,571,120 A | | 11/1996 | Yoon | |
| 5,573,540 A | * | 11/1996 | Yoon | 606/139 |
| 5,609,597 A | | 3/1997 | Lehrer | |
| 5,613,974 A | | 3/1997 | Andreas et al. | |
| 5,613,975 A | | 3/1997 | Christy | |
| 5,643,318 A | | 7/1997 | Tsukernik et al. | |
| 5,647,372 A | | 7/1997 | Tovey et al. | |
| 5,649,959 A | | 7/1997 | Hannam et al. | |
| 5,669,935 A | | 9/1997 | Rosenman et al. | |
| 5,672,174 A | | 9/1997 | Gough et al. | |
| 5,674,231 A | | 10/1997 | Green et al. | |
| 5,693,061 A | | 12/1997 | Pierce et al. | |
| 5,713,899 A | | 2/1998 | Marnay et al. | |
| 5,728,143 A | | 3/1998 | Gough et al. | |
| 5,735,736 A | | 4/1998 | Volk | |
| 5,749,898 A | | 5/1998 | Schulze et al. | |
| 5,759,189 A | | 6/1998 | Ferragamo et al. | |
| 5,766,217 A | * | 6/1998 | Christy | 606/148 |
| 5,782,861 A | * | 7/1998 | Cragg et al. | 606/216 |
| 5,792,151 A | * | 8/1998 | Heck et al. | 606/144 |
| 5,797,928 A | | 8/1998 | Kogasaka | |
| 5,797,929 A | | 8/1998 | Andreas et al. | |
| 5,810,845 A | * | 9/1998 | Yoon | 606/139 |
| 5,814,052 A | * | 9/1998 | Nakao et al. | 606/115 |
| 5,817,113 A | | 10/1998 | Gifford, III et al. | |
| 5,845,657 A | | 12/1998 | Carberry et al. | |
| 5,855,576 A | | 1/1999 | LeVeen et al. | |
| 5,861,005 A | | 1/1999 | Kontos | |
| 5,865,791 A | * | 2/1999 | Whayne et al. | 604/500 |
| 5,873,876 A | | 2/1999 | Christy | |
| 5,897,487 A | * | 4/1999 | Ouchi | 600/127 |
| 5,906,620 A | | 5/1999 | Nakao et al. | |
| 5,906,631 A | | 5/1999 | Imran | |
| 5,919,207 A | * | 7/1999 | Taheri | 606/219 |
| 5,944,728 A | | 8/1999 | Bates | |
| 5,951,547 A | | 9/1999 | Gough et al. | |
| 5,957,936 A | * | 9/1999 | Yoon et al. | 606/144 |
| 5,957,938 A | | 9/1999 | Zhu et al. | |
| 5,964,782 A | * | 10/1999 | Lafontaine et al. | 606/213 |
| 5,972,009 A | | 10/1999 | Fortier et al. | |
| 5,976,161 A | | 11/1999 | Kirsch et al. | |
| 5,980,517 A | | 11/1999 | Gough et al. | |
| 5,984,950 A | | 11/1999 | Cragg et al. | |
| 5,993,466 A | | 11/1999 | Yoon | |
| 5,993,476 A | | 11/1999 | Groiso | |
| 6,009,877 A | | 1/2000 | Edwards | |
| 6,022,372 A | | 2/2000 | Kontos | |
| 6,024,747 A | | 2/2000 | Kontos | |
| 6,056,744 A | | 5/2000 | Edwards | |
| 6,059,719 A | | 5/2000 | Yamamoto et al. | |
| 6,068,603 A | * | 5/2000 | Suzuki | 600/565 |
| 6,083,242 A | | 7/2000 | Cook | |
| 6,095,155 A | | 8/2000 | Criscuolo | |
| 6,120,513 A | | 9/2000 | Bailey et al. | |
| 6,120,524 A | | 9/2000 | Taheri | |
| 6,126,675 A | | 10/2000 | Shchervinsky et al. | |
| 6,136,010 A | | 10/2000 | Modesitt et al. | |
| 6,143,004 A | | 11/2000 | Davis et al. | |
| 6,152,936 A | * | 11/2000 | Christy et al. | 606/148 |
| 6,161,263 A | | 12/2000 | Anderson | |
| 6,165,204 A | | 12/2000 | Levinson et al. | |
| 6,178,355 B1 | | 1/2001 | Williams et al. | |
| 6,197,042 B1 | | 3/2001 | Ginn et al. | |
| 6,221,084 B1 | | 4/2001 | Fleenor | |
| 6,248,124 B1 | | 6/2001 | Pedros et al. | |
| 6,296,657 B1 | | 10/2001 | Brucker | |
| 6,306,081 B1 | | 10/2001 | Ishikawa et al. | |
| 6,322,580 B1 | | 11/2001 | Kanner | |
| 6,358,258 B1 | | 3/2002 | Arcia et al. | |
| 6,395,015 B1 | | 5/2002 | Borst et al. | |
| 6,397,110 B1 | | 5/2002 | Kuzma | |
| 6,428,472 B1 | | 8/2002 | Haas | |
| 6,443,963 B1 | | 9/2002 | Baldwin et al. | |
| 6,461,366 B1 | | 10/2002 | Seguin | |
| 6,482,224 B1 | | 11/2002 | Michler et al. | |
| 6,506,209 B2 | | 1/2003 | Ouchi | |
| 6,517,498 B1 | | 2/2003 | Burbank et al. | |
| 6,533,812 B2 | | 3/2003 | Swanson et al. | |
| 6,547,806 B1 | | 4/2003 | Ding | |
| 6,569,159 B1 | | 5/2003 | Edwards et al. | |
| 6,569,185 B2 | | 5/2003 | Ungs | |
| 6,572,629 B2 | | 6/2003 | Kalloo et al. | |
| 6,578,585 B1 | | 6/2003 | Stachowski et al. | |
| 6,599,311 B1 | | 7/2003 | Biggs et al. | |
| 6,610,072 B1 | | 8/2003 | Christy et al. | |
| 6,613,060 B2 | | 9/2003 | Adams et al. | |
| 6,623,509 B2 | | 9/2003 | Ginn | |
| 6,623,510 B2 | | 9/2003 | Carley et al. | |
| 6,663,655 B2 | | 12/2003 | Ginn et al. | |
| 6,676,685 B2 | | 1/2004 | Pedros et al. | |
| 6,679,904 B2 | | 1/2004 | Gleeson et al. | |
| 6,689,051 B2 | | 2/2004 | Nakada et al. | |

(56) References Cited

U.S. PATENT DOCUMENTS

| | | |
|---|---|---|
| 6,695,867 B2 | 2/2004 | Ginn et al. |
| 6,736,822 B2 | 5/2004 | McClellan et al. |
| 6,743,195 B2 | 6/2004 | Zucker |
| 6,743,259 B2 | 6/2004 | Ginn |
| 6,745,079 B2 | 6/2004 | King |
| 6,746,457 B2 | 6/2004 | Dana et al. |
| 6,749,621 B2 | 6/2004 | Pantages et al. |
| 6,749,622 B2 | 6/2004 | McGuckin, Jr. et al. |
| 6,767,356 B2 | 7/2004 | Kanner et al. |
| 6,776,785 B1 | 8/2004 | Yencho et al. |
| 6,837,906 B2 | 1/2005 | Ginn |
| 6,846,319 B2 | 1/2005 | Ginn et al. |
| 6,849,078 B2 | 2/2005 | Durgin et al. |
| 6,890,343 B2 | 5/2005 | Ginn et al. |
| 6,896,692 B2 | 5/2005 | Ginn et al. |
| 6,904,647 B2 | 6/2005 | Byers, Jr. |
| 6,942,674 B2 | 9/2005 | Belef et al. |
| 6,969,397 B2 | 11/2005 | Ginn |
| 6,984,238 B2 | 1/2006 | Gifford, III et al. |
| 7,048,747 B2 | 5/2006 | Arcia et al. |
| 7,060,084 B1 | 6/2006 | Lashakove et al. |
| 7,063,661 B2 | 6/2006 | Okada |
| 7,063,711 B1 | 6/2006 | Loshakove et al. |
| 7,083,635 B2 | 8/2006 | Ginn |
| 7,112,225 B2 | 9/2006 | Ginn |
| 7,122,002 B2 | 10/2006 | Okada |
| 7,147,646 B2 | 12/2006 | Dana et al. |
| 7,270,672 B1 | 9/2007 | Singer |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,338,514 B2 | 3/2008 | Wahr et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,507,200 B2 | 3/2009 | Okada |
| 7,645,285 B2 | 1/2010 | Cosgrove et al. |
| 7,648,493 B2 | 1/2010 | Forsberg et al. |
| 7,727,249 B2 | 6/2010 | Rahmani |
| 7,731,655 B2 * | 6/2010 | Smith et al. ............. 600/217 |
| 7,749,249 B2 | 7/2010 | Gelbart et al. |
| 7,799,042 B2 | 9/2010 | Williamson, IV et al. |
| 7,901,428 B2 | 3/2011 | Ginn et al. |
| 8,226,666 B2 | 7/2012 | Zarbatany et al. |
| 8,313,497 B2 | 11/2012 | Walberg et al. |
| 8,469,969 B2 | 6/2013 | Kear et al. |
| 8,480,687 B2 | 7/2013 | Ducharme et al. |
| 2001/0046518 A1 | 11/2001 | Sawhney |
| 2001/0053909 A1 | 12/2001 | Nakada |
| 2002/0099389 A1 | 7/2002 | Michler et al. |
| 2002/0106409 A1 | 8/2002 | Sawhney et al. |
| 2002/0188275 A1 | 12/2002 | McGuckin, Jr. |
| 2003/0187457 A1 * | 10/2003 | Weber ............. 606/110 |
| 2003/0233095 A1 | 12/2003 | Urbanski et al. |
| 2004/0009205 A1 | 1/2004 | Sawhney |
| 2004/0093027 A1 | 5/2004 | Fabisiak et al. |
| 2004/0098044 A1 | 5/2004 | Van de Moer et al. |
| 2004/0116943 A1 | 6/2004 | Brandt et al. |
| 2004/0122349 A1 | 6/2004 | Lafontaine et al. |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0191277 A1 | 9/2004 | Sawhney et al. |
| 2004/0215232 A1 | 10/2004 | Belhe et al. |
| 2004/0225194 A1 | 11/2004 | Smith et al. |
| 2004/0236354 A1 | 11/2004 | Seguin |
| 2004/0267193 A1 | 12/2004 | Bagaoisan et al. |
| 2004/0267308 A1 | 12/2004 | Bagaoisan et al. |
| 2005/0010248 A1 | 1/2005 | Lafontaine |
| 2005/0033359 A1 | 2/2005 | Dycus |
| 2005/0075665 A1 * | 4/2005 | Brenzel et al. ............. 606/213 |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0121042 A1 * | 6/2005 | Belhe et al. ............. 128/887 |
| 2005/0149117 A1 | 7/2005 | Khosravi et al. |
| 2005/0177189 A1 | 8/2005 | Ginn et al. |
| 2005/0222614 A1 | 10/2005 | Ginn et al. |
| 2005/0234396 A1 | 10/2005 | Forsberg et al. |
| 2005/0245876 A1 | 11/2005 | Khosravi et al. |
| 2005/0256532 A1 * | 11/2005 | Nayak et al. ............. 606/151 |
| 2005/0261708 A1 * | 11/2005 | Pasricha et al. ............. 606/139 |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0106420 A1 | 5/2006 | Dolan et al. |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0083231 A1 | 4/2007 | Lee |
| 2007/0123817 A1 | 5/2007 | Khosravi et al. |
| 2007/0123936 A1 | 5/2007 | Goldin et al. |
| 2007/0198058 A1 | 8/2007 | Gelbart et al. |
| 2007/0203506 A1 | 8/2007 | Sibbitt, Jr. et al. |
| 2007/0213747 A1 | 9/2007 | Monassevitch et al. |
| 2008/0009794 A1 | 1/2008 | Bagaoisan et al. |
| 2008/0045979 A1 | 2/2008 | Ma |
| 2008/0065151 A1 | 3/2008 | Ginn |
| 2008/0065152 A1 | 3/2008 | Carley |
| 2008/0287967 A1 | 11/2008 | Andreas et al. |
| 2008/0287988 A1 | 11/2008 | Smith et al. |
| 2009/0088794 A1 | 4/2009 | LaFontaine |
| 2009/0105728 A1 | 4/2009 | Noda et al. |
| 2009/0157101 A1 | 6/2009 | Reyes et al. |
| 2009/0254119 A1 | 10/2009 | Sibbitt, Jr. et al. |
| 2010/0234884 A1 | 9/2010 | Lafontaine et al. |
| 2011/0066163 A1 | 3/2011 | Cho et al. |
| 2012/0245603 A1 | 9/2012 | Voss |
| 2012/0296374 A1 | 11/2012 | Ziobro et al. |

FOREIGN PATENT DOCUMENTS

| | | |
|---|---|---|
| JP | 2005218868 A | 8/2005 |
| WO | WO 96/40356 | 12/1996 |
| WO | WO 00/56226 | 9/2000 |
| WO | WO 02/062234 | 8/2002 |
| WO | WO 03/094748 | 11/2003 |
| WO | WO 2005/000126 | 1/2005 |
| WO | WO 2005/041782 | 5/2005 |
| WO | WO 2005/063129 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |
| WO | WO 2006/118877 | 11/2006 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2010/031050 | 3/2010 |

OTHER PUBLICATIONS

U.S. Appl. No. 60/726,985, filed Oct. 14, 2005, Sibbitt Jr. et al.

(56) References Cited

OTHER PUBLICATIONS

U.S. Appl. No. 61/097,072, filed Sep. 16, 2008, Sibbitt Jr. et al.
U.S. Appl. No. 11/316,775, Apr. 16, 2008, Office Action.
U.S. Appl. No. 11/316,775, Aug. 6, 2008, Office Action.
U.S. Appl. No. 11/508,656, Dec. 9, 2009, Office Action.
U.S. Appl. No. 11/508,656, Mar. 25, 2010, Office Action.
U.S. Appl. No. 11/508,656, Aug. 30, 2010, Office Action.
U.S. Appl. No. 11/508,662, Dec. 28, 2009, Office Action
U.S. Appl. No. 11/508,662, Apr. 14, 2010, Office Action.
U.S. Appl. No. 11/508,662, Oct. 26, 2010, Office Action.
U.S. Appl. No. 11/508,715, Apr. 26, 2010, Office Action.
U.S. Appl. No. 11/508,715, Jan. 6, 2010, Office Action.
U.S. Appl. No. 11/508,715, Oct. 18, 2010, Office Action.
U.S. Appl. No. 12/365,397, Sep. 13, 2010, Office Action.
U.S. Appl. No. 12/365,397, Dec. 17, 2010, Office Action.
U.S. Appl. No. 12/365,397, Jun. 21, 2011, Notice of Allowance.
U.S. Appl. No. 11/508,656, Feb. 10, 2014, Notice of Allowance.
U.S. Appl. No. 11/508,662, Mar. 24, 2014, Office Action.
U.S. Appl. No. 11/508,715, Mar. 27, 2014, Office Action.
U.S. Appl. No. 13/052,634, Feb. 8, 2013, Restriction Requirement.
U.S. Appl. No. 13/052,634, Apr. 22, 2013, Office Action.
U.S. Appl. No. 13/052,634, Nov. 8, 2013, Office Action.
U.S. Appl. No. 13/111,403, Jun. 28, 2013, Restriction Requirement.
U.S. Appl. No. 13/111,403, Sep. 5, 2013, Office Action.
U.S. Appl. No. 13/111,403, Dec. 24, 2013, Office Action.
U.S. Appl. No. 11/508,656, Jun. 4, 2014, Issue Notification.
U.S. Appl. No. 11/508,662, Jul. 25, 2014, Notice of Allowance.

* cited by examiner

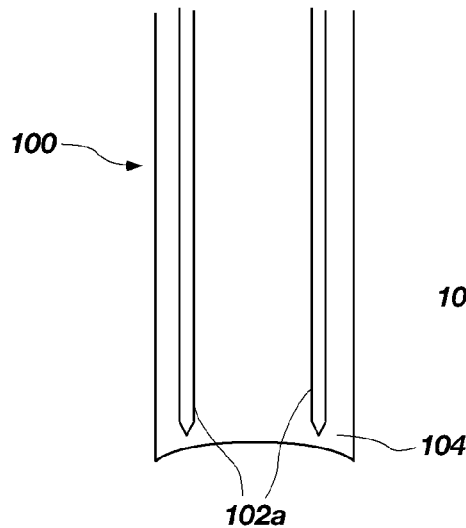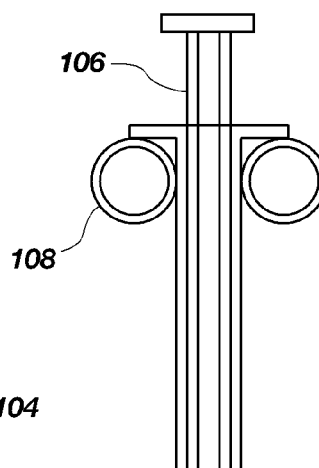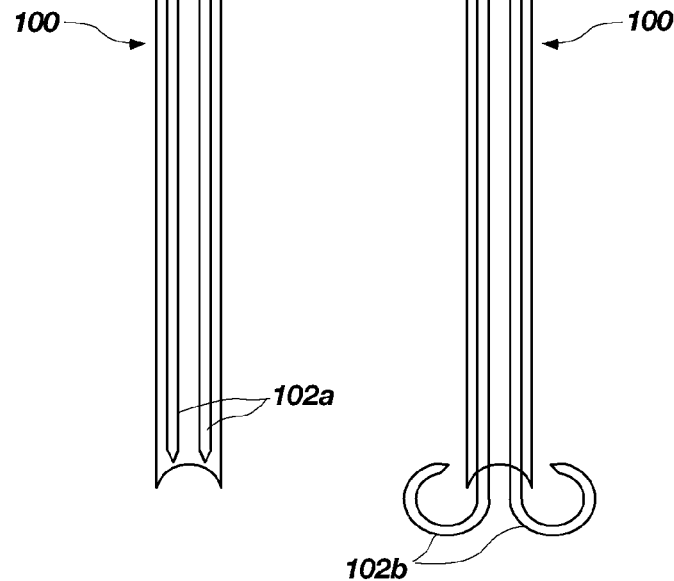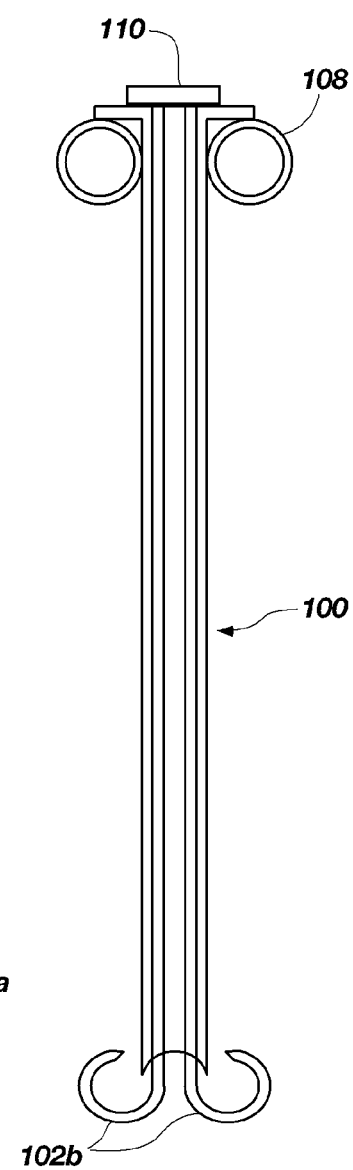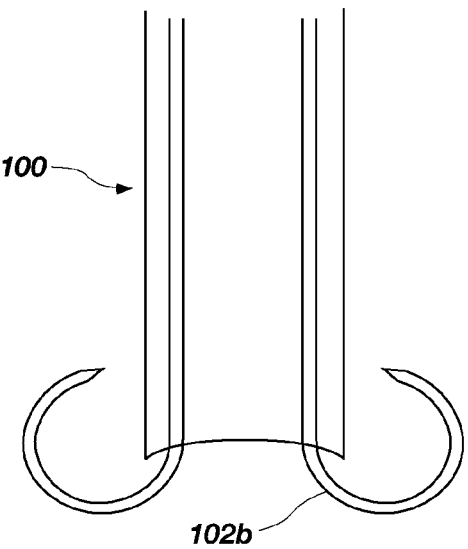
FIG. 1A
FIG. 1B
FIG. 1C
FIG. 1D

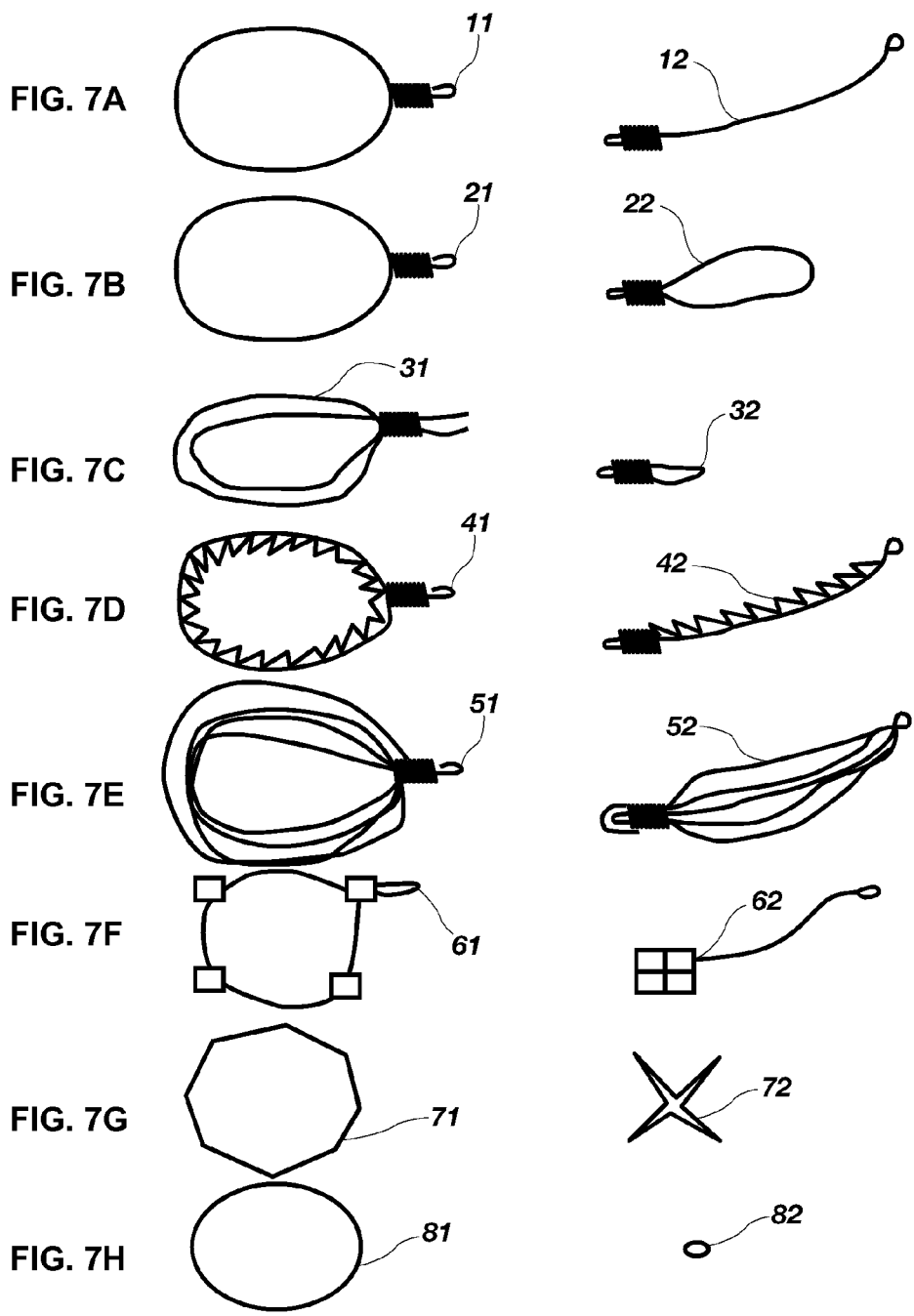

REDUNDANT TISSUE CLOSURE METHODS AND APPARATUSES

CROSS-REFERENCE TO RELATED APPLICATIONS

This application claims the benefit of and priority to U.S. Provisional Pat. App. No. 61/097,072, filed 15 Sep. 2008, entitled "REDUNDANT TISSUE CLOSURE METHODS AND APPARATUSES." This application is a continuation of U.S. patent application Ser. No. 12/365,397, filed 4 Feb. 2009, now U.S. Pat. No. 8,048,108, entitled "VASCULAR CLOSURE METHODS AND APPARATUSES," which is a continuation of U.S. patent application Ser. No. 11/316,775, filed 23 Dec. 2005, entitled "VASCULAR CLOSURE METHODS AND APPARATUSES," now abandoned, which claims the benefit of and priority to U.S. Provisional App. No. 60/711,279, filed 24 Aug. 2005, entitled "VASCULAR CLOSURE METHODS AND APPARATUSES." This application is a continuation-in-part of U.S. patent application Ser. No. 11/508,656, filed 23 Aug. 2006, entitled "VASCULAR CLOSURE METHODS AND APPARATUSES," which claims the benefit of and priority to U.S. Provisional Pat. App. No. 60/711,279, filed 24 Aug. 2005, entitled "VASCULAR CLOSURE METHODS AND APPARATUSES," and which is a continuation-in-part of U.S. patent application Ser. No. 11/316,775, filed 23 Dec. 2005, entitled, "VASCULAR CLOSURE METHODS AND APPARATUSES," now abandoned, which claims the benefit of and priority to U.S. Provisional Pat. App. No. 60/711,279, filed 24 Aug. 2005, entitled "VASCULAR CLOSURE METHODS AND APPARATUSES." This application is a continuation-in-part of U.S. patent application Ser. No. 11/508,715, filed 23 Aug. 2006, entitled "VASCULAR CLOSURE METHODS AND APPARATUSES," which claims the benefit of and priority to U.S. Provisional Pat. App. No. 60/711,279, filed 24 Aug. 2005, entitled "VASCULAR CLOSURE METHODS AND APPARATUSES," and which is a continuation-in-part of U.S. patent application Ser. No. 11/316,775, filed 23 Dec. 2005, entitled, "VASCULAR CLOSURE METHODS AND APPARATUSES," now abandoned, which claims the benefit of and priority to U.S. Provisional Pat. App. No. 60/711,279, filed 24 Aug. 2005, entitled "VASCULAR CLOSURE METHODS AND APPARATUSES." This application is a continuation-in-part of U.S. patent application Ser. No. 11/508,662, filed 23 Aug. 2006, entitled "VASCULAR OPENING EDGE EVERSION METHODS AND APPARATUSES," which claims the benefit of and priority to U.S. Provisional Pat. App. No. 60/711,279, filed 24 Aug. 2005, entitled "VASCULAR CLOSURE METHODS AND APPARATUSES," and claims benefit of and priority to U.S. Provisional Pat. App. No. 60/726,985, filed 14 Oct. 2005, entitled "SEALANT PLUG SYRINGES, TUBES, AND PENCILS," and which is a continuation-in-part of U.S. patent application Ser. No. 11/316,775, filed 23 Dec. 2005, entitled, "VASCULAR CLOSURE METHODS AND APPARATUSES," now abandoned, which claims the benefit of and priority to U.S. Provisional Pat. App. No. 60/711,279, filed 24 Aug. 2005, entitled "VASCULAR CLOSURE METHODS AND APPARATUSES." The entire disclosures of each of the above are hereby incorporated by reference in their entirety.

BACKGROUND

1. The Field of the Invention

The present disclosure relates to tissue closure apparatuses and methods.

2. The Relevant Technology

During intravascular and other related procedures, catheters are typically inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, stent delivery, plaque removal, and infusion of a therapeutic substance. After the procedure is completed and the catheter is removed from the patient, however, the access hole must be closed to prevent massive hemorrhage. This is typically achieved by applying pressure over the blood vessel manually and then by applying a pressure bandage or a compressive weight. With conventional methods, the rate of post-puncture hemorrhage is high, which can cause considerable complications. This complication is exacerbated by the concomitant use of anticoagulant medications such as heparin or warfarin and by anti-platelet drugs, which are commonly used following a procedure in order to prevent clot formation and thrombus and/or to treat vascular disease.

It is generally recognized that many currently employed vascular sealing methods and devices and other tissue closure methods and devices have an inherent failure rate due to incomplete sealing of holes or wounds in vascular or other tissue. Achieving complete wound closure is particularly important in sealing arterial punctures, which are relatively high pressure systems. For example, under normal blood pressure, the arterial system has a pressure of about 120/80 mmHg or more. Failure to completely close arterial holes can result in hematoma, exsanguination, and other catastrophic consequences, including limb amputation and death. Moreover, many currently employed vascular devices employ methods and materials that remain on the intravascular endothelial surface or otherwise in the sealed vessel. Materials that remain intravascularly can be a nidus for thrombus or intravascular mural hyperplasia with later spontaneous and catastrophic closure of the vessel.

BRIEF SUMMARY

The present disclosure provides methods and apparatuses that are suitable for closure of vascular punctures or other openings in bodily tissues. The apparatuses and methods disclosed herein provide a redundancy of closure, which enhances wound healing and patient safety. The devices and methods described herein are configured for wound closure on the external surface of the wound, which allows wound healing with little endothelial disruption thereby reducing the chances of intravascular thrombosis or embolism or intimal hyperplasia.

The present disclosure describes a closure device for closing an opening in a tissue. An exemplary tissue closure device according to the present disclosure includes at least one tubular member, a tissue eversion apparatus configured to form an everted tissue region around the opening in the tissue, a first closure element, which can be deployed over the tissue opening around the portion of everted tissue, and a second, redundant closure element that is applied in addition to the first closure element to ensure efficient closure. Combining a first closure and a second, redundant closure provides for wound closure with a failure rate and/or complication rate lower than either acting alone. The devices described herein can be supplied in different diameters (e.g., French sizes) to accommodate different sizes of catheters and different sizes of puncture holes.

The tissue eversion apparatus, the first closure element, and the second closure element are typically disposed in a lumen of one or more tubular members and deployable therefrom. The tubular members can be sheaths having various shapes and/or be formed from various materials, as examples a solid walled or porous walled cylinder or other shape, or a plurality of guide rods or bars mounted relative to each other.

The present disclosure also describes methods for closing an opening in a tissue using, for example, an embodiment of an apparatus as described above. Tissue openings can include openings in a body lumen such as an opening in a blood vessel. An exemplary method for closing an opening in a tissue includes (a) deploying a tissue eversion apparatus into the opening in the body lumen, the tissue eversion apparatus having a plurality of elongate tissue engaging members capable of approximating and everting edges of the opening to form an everted tissue region, (b) deploying a first closure element in a first configuration to the everted tissue region around the opening in the body lumen, (c) transitioning the first closure element that was disposed around the portion of everted tissue to a second, smaller configuration so as to close the opening in the body lumen, (d) retracting the tissue eversion apparatus so as to release the everted edges, and (e) deploying a second closure element over or around the first closure element so as to redundantly close the opening in the body lumen.

According to the present disclosure, the act of deploying a second closure element over or around the first closure element can be performed either before or after retracting the tissue eversion apparatus so as to release the everted edges.

According to the present disclosure, the first closure element can include a cincture element having a first size and a second size that is smaller than the first size. Accordingly, the first size is configured to surround a portion of the everted tissue region around the opening and the second size is configured to capture a portion of the everted tissue region and close the opening when the cincture element is transitioned from the first size towards and/or to the second size.

In one embodiment, the cincture element includes a loop of suture having at least one pre-tied knot, such that the loop can be tightened by pulling on a free-end so as to close the loop and close the tissue opening. In one embodiment, the pre-tied knot can be, for example, a slip knot. In one embodiment, the loop of suture can include at least one dentate configured to maintain the cincture element in a closed position. That is, the at least one dentate can permit the loop to be pulled closed while simultaneously functioning to prevent re-opening of the loop.

In one embodiment, the cincture element can be formed from a shape memory material having an expanded delivery configuration and a contracted deployed configuration. For instance, the shape memory cincture element can be a ring-like structure formed from a metallic material (e.g., NiTi) or a polymeric material (e.g., a rubber-like material) that resiliently closes the opening when the first closure element is deployed around the everted tissue region. The shape memory cincture element may be biased towards the contracted deployed configuration.

Suitable examples of second closure elements that can be applied to the wound after the first closure element is placed can include, but are not limited to, sealant plugs, adhesive glues, occlusive substances, extraluminal clips, RF energy, thermal energy, electrical induction, infrared light, ultrasonic vibration, microwave or laser irradiation, sutures, and combinations thereof.

These and other objects and features of the present disclosure will become more fully apparent from the following description and appended claims, or may be learned by the practice of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 1A-1D illustrate schematic views of a tissue eversion apparatus according to one embodiment of the present disclosure.

FIGS. 7A-7H schematically illustrate a number of tissue cinctures that can be used to close an opening according to one embodiment of the present disclosure.

DETAILED DESCRIPTION

Figure 2A:
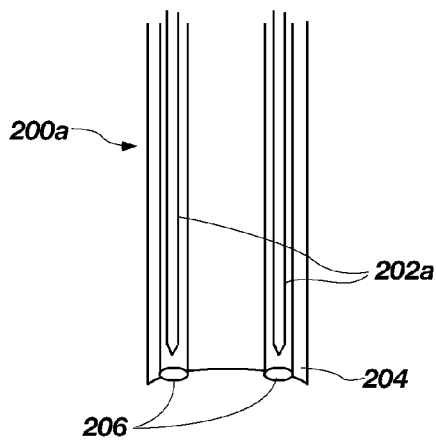
FIGS. 2A-2D illustrate schematic views of a tissue eversion apparatus according to several embodiments of the present disclosure.

The present disclosure provides apparatuses and methods for closing a vascular puncture wound or any tissue aperture, for example those resulting from the insertion of a vascular catheter or surgical instrument, trauma or disease. The apparatuses and methods disclosed herein provide a redundancy of closure, which enhances wound healing and patient safety. The devices and methods described herein are configured for wound closure on the external surface of the wound, which allows wound healing with little endothelial disruption and thereby reducing the chances of intravascular thrombosis or embolism or intimal hyperplasia.

The description included herein refers to "vessels" for convenience; the present disclosure is applicable to facilitate closure of various types of tissue openings.

The present disclosure describes a closure device for closing an opening in a tissue. An exemplary tissue closure device according to the present disclosure includes at least one tubular member, a tissue eversion apparatus configured to form an everted tissue region around the opening in the tissue, a first closure element, which can be deployed over the tissue opening around the portion of everted tissue, and a second, redundant closure element that is applied in addition to the first closure element to ensure efficient closure.

Referring now to FIGS. 1A-1D, schematic illustrations of a tissue eversion apparatus 100 according to one embodiment of the present disclosure are shown. FIG. 1A is a lateral, cutaway view of a tissue eversion apparatus 100 in a closed or undeployed state. A plurality of tissue engaging members 102a are shown in a retracted state disposed in an elongate tubular sheath member 104. As shown in a non-limiting example in FIG. 1A, two tissue engaging members 102a are disposed in the sheath 104. However, any practical number of tissue engaging members 102a can be disposed in the sheath 104 such that the tissue engaging members 102a can engage with or otherwise grasp tissue surrounding an opening when the tissue engaging members 102a are deployed. The elongate tubular sheath member 104 is configured to accommodate a guidewire, or in another embodiment can be inserted through a sheath or a closure device and used like a guidewire.

FIG. 1B is a lateral, cutaway view of the tissue eversion apparatus 100 in an extended or deployed state, where the tissue engaging members 102b are extended. As shown in FIG. 1B, the tissue engaging members 102b can curl up when they are in the extended position. In one embodiment, the tissue engaging members can be formed from a shape-memory material such as a nickel-titanium alloy to facilitate the shape change from the retracted to the deployed state.

In another embodiment, the tissue engaging members can be formed from a deformable material, such that the tissue engaging members can bent for disposal in the delivery sheath. For example, the tissue engaging members can include a sharp bend that directs the distal ends of the tissue engaging members toward the proximal end of the delivery sheath. When the tissue engaging members are deployed out of the delivery sheath, the pre-bent shape allows the tissue engaging members to engage with the vessel walls. In yet another embodiment, the tissue engaging members can include hinged members near the distal ends of the engaging members. The hinges can be configured to allow the tissue engaging members to be folded for disposal in the delivery sheath and the hinges can be configured to allow the distal ends of the engaging members to splay out and engage with the vessel walls when the engaging members are deployed into the vessel lumen.

FIG. 1C is a lateral view showing the tissue eversion apparatus 100 in the retracted state with a plunger mechanism 106 that can be used to extend the tissue engaging members 102a and finger flanges or rests 108 to control the device. FIG. 1D is a lateral view showing the tissue eversion apparatus 100 in the deployed state.

The tissue eversion apparatus 100 shown in FIGS. 1A-1D can be guided or placed into a puncture wound by means of a guidewire that can be accommodated within the sheath 104. The tissue eversion apparatus shown in FIGS. 1A-1D can be placed into the puncture wound by means of a sheath that can accommodate the everter device 100 internally. The tissue eversion apparatus shown in FIGS. 1A-1D can be placed into the puncture wound using other methods. Regardless, once the tissue eversion apparatus 100 is in the vessel, the tissue engaging members 102 can be deployed and used to evert the tissue around the opening or wound.

FIGS. 2A-2D illustrate alternative embodiments of a tissue eversion apparatus 200, according to the present disclosure. FIG. 2A is a lateral cutaway view of a tissue eversion apparatus 200a with tissue engaging members 202a in a retracted state. In the embodiment shown in FIG. 2A, tissue engaging members 202a are retracted within internal lumens 206 that are disposed within lumen 204.

Figure 2B:
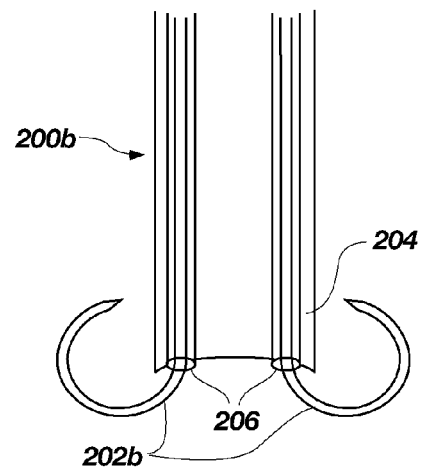
Figure 2C:
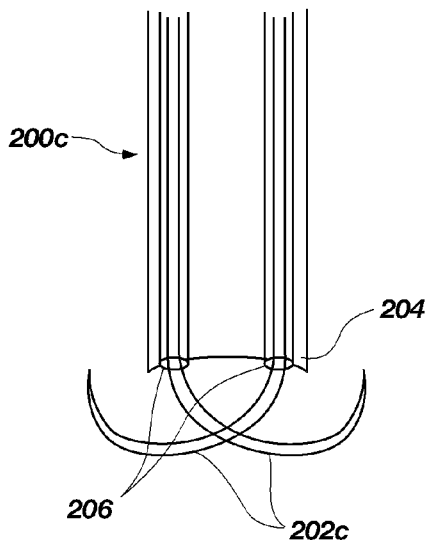
Figure 2D:
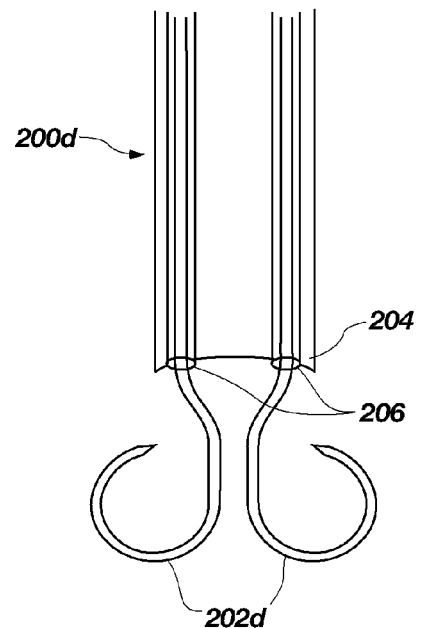

FIG. 2B is a lateral view of a tissue eversion apparatus 200b in the extended or opened state, where the tissue engaging members 202b are extended, and curl up to allow engagement with a vessel wall. FIG. 2C is another schematic illustration of a tissue eversion apparatus 200c. As shown in FIG. 2C, the tissue engaging members 202c extend in a cross-wise function across the sheath 204, the purpose being that the wound edges can be more efficiently and mechanically brought into apposition by the tissue engaging members 202c when members 200c engage with the tissue around the wound and the device 200c is retracted from the wound in order to draw the tissue up and form a portion of everted tissue. FIG. 2D is another schematic illustration of a tissue eversion apparatus 200d. As shown in FIG. 2D, the tissue engaging members 202d extend towards one another towards the central axis of the sheath 204, the purpose being that the wound edges can be more efficiently and mechanically brought into apposition by the tissue engaging members 202d when members 200d engage with the tissue around the wound and the device 200d is retracted from the wound in order to draw the tissue up and form a portion of everted tissue.

In the embodiments illustrated herein the plurality of tissue engaging members are shown as separate elongate members. One will appreciate, however, that the plurality of members can be coupled together at a point proximal to the distal ends of each of the individual tissue engaging members. For example, the plurality of members can be coupled to an elongate columnar member that can allow the tissue engaging members to be deployed and retracted. Coupling the tissue engaging members proximal to their ends can also be advantageous in that it can reduce the diameter of the tissue region everted by the engaging members in a manner similar to what is shown in FIG. 2D.

FIGS. 1A-2D present for illustration purposes two tissue engaging members; the devices shown can include as few as two tissue engaging members, but can include any plurality, and as many as are practical within applicable design considerations. The tissue engagement features (e.g., 102a), shown as sharp hook-like portions of the active members in the figure, can include textured portions or attachments, mating portions with apposing feet, penetrating devices, hooks, teeth, or other adaptations to allow firm engagement of the tissue.

Additional discussion of tissue eversion apparatuses that can be adapted for use in the devices and methods discussed herein can be found in U.S. patent application Ser. No. 11/316,775, filed 23 Dec. 2005, now abandoned, entitled "VASCULAR CLOSURE METHODS AND APPARATUSES" and U.S. patent application Ser. No. 11/508,662, filed 23 Aug. 2006, entitled "VASCULAR OPENING EDGE EVERSION METHODS AND APPARATUSES," the entireties of which are incorporated herein by reference.

Figure 3A:
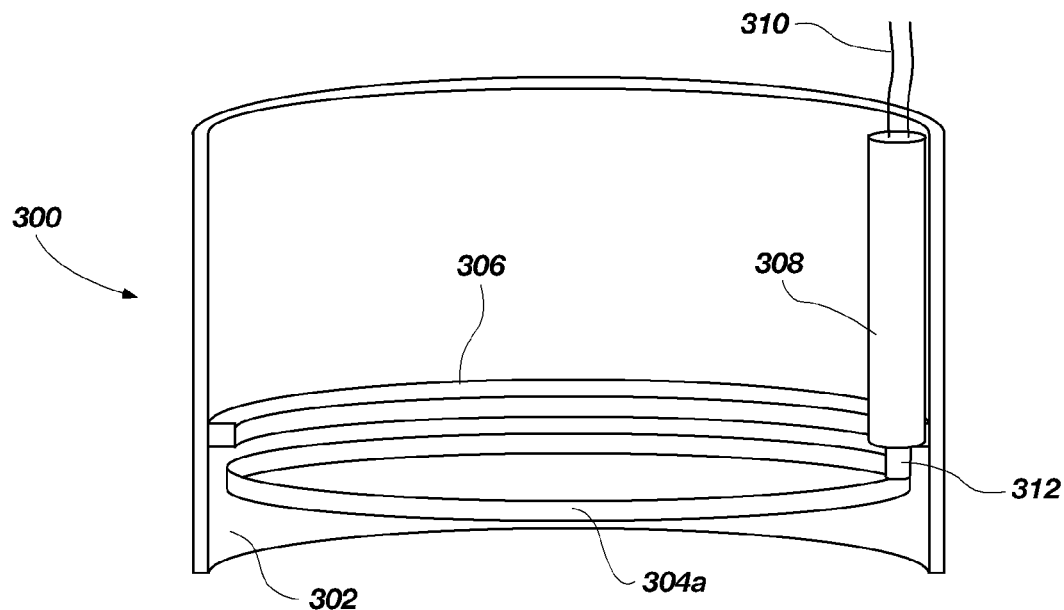
FIGS. 3A and 3B illustrate a tissue cincture apparatus according to one embodiment of the present disclosure.
Figure 3B:
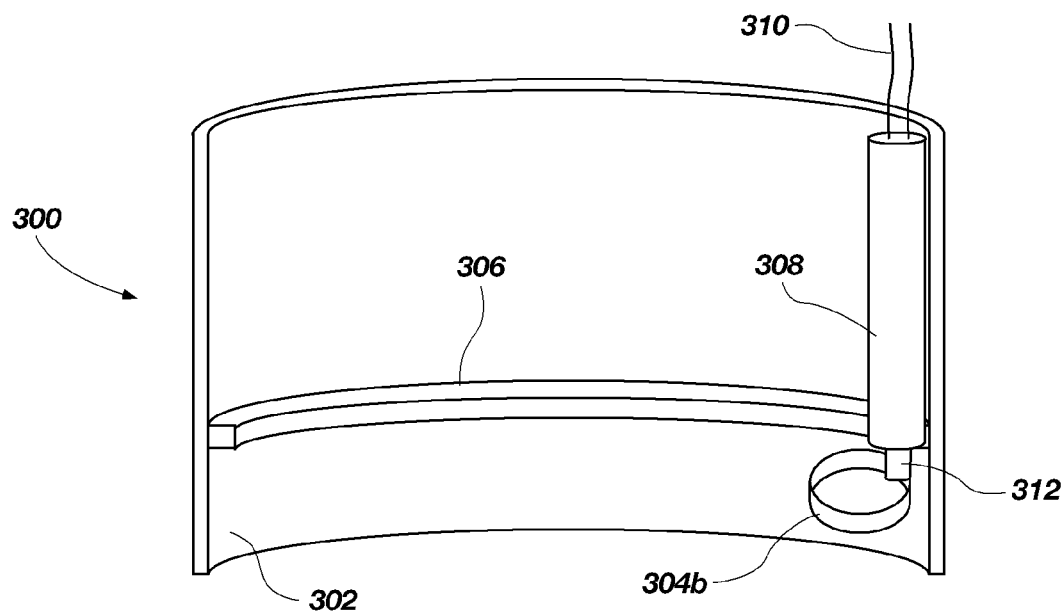

FIGS. 3A and 3B illustrate a cincture apparatus 300 according to one embodiment of the present disclosure. The cincture apparatus 300 includes a tubular member 302 (e.g., a delivery sheath) and a cincture (shown as 304a in FIGS. 3A and 304b in FIG. 3B) disposed in the lumen of tubular member 302. The cincture shown in FIGS. 3A and 3B is transitionable from an open configuration 304a to a contracted or closed configuration 304b. The cincture apparatus 300 shown in FIGS. 3A and 3B can be used in conjunction with the tissue eversion apparatuses discussed above to deliver a closure element (such as cincture 304a, 304b) to a portion of everted tissue according to the devices and methods disclosed herein.

Referring to FIG. 3A, the interior wall of the delivery sheath 302 delivers a cincture 304a, which can be held in place in the sheath 302 by a retention structure 306. The retention structure 306 can prevent the cincture 304a from malpositioning and/or from prematurely contracting. The cincture 304a, which can be held by the retention structure 306, can be sufficiently rigid to not readily change position and/or can be temporarily held in place by a wax-like or other semi-solid biocompatible material that will give way with contraction of the cincture 304a.

The cincture 304a can be attached to a retractable suture loop 310, which is contained in a lumen 308, shown in the Figure as a cylindrical structure. The lumen 308 can include a narrowed portion 312 that permits the cincture material to pass, but prevents a tightening feature (e.g., a functional slip-knot) from passing. Thus when the suture loop 310 is pulled, the cincture 304a is reduced in diameter and transitioned towards and/or to the smaller diameter 304b. When the suture loop 310 is pulled in its entirety, the cincture loop 304b completely closes, effecting closure around a portion of everted tissue around an opening (e.g., a puncture wound).

Figure 4A:
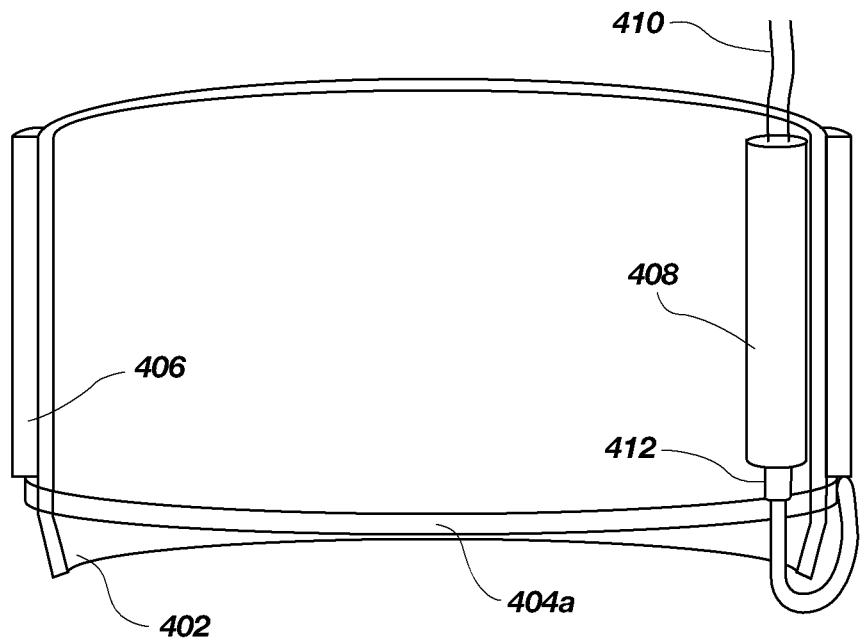
FIGS. 4A and 4B illustrate a tissue cincture apparatus according to one embodiment of the present disclosure.
Figure 4B:
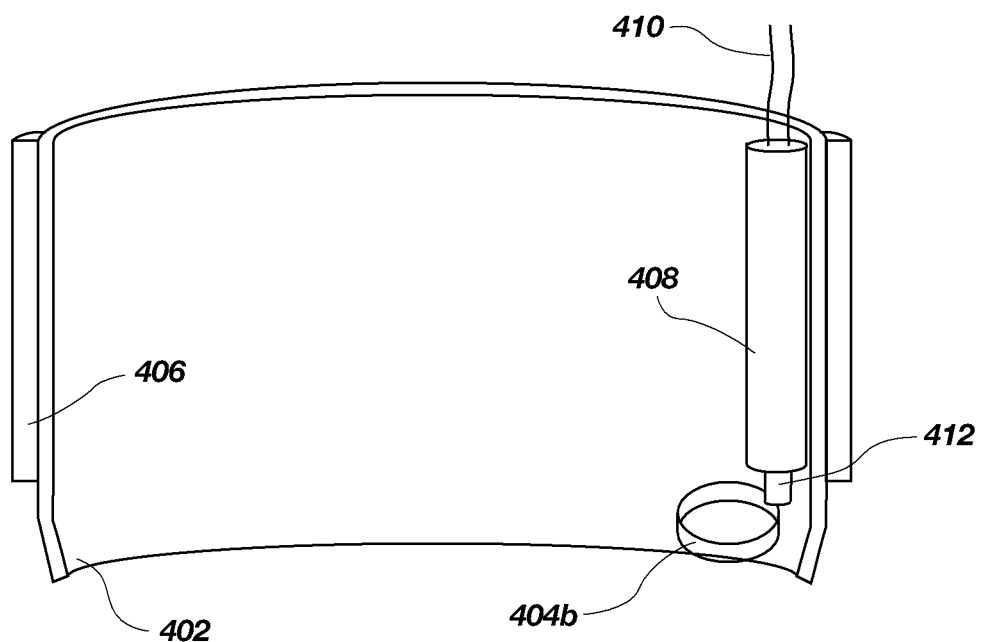

FIGS. 4A and 4B illustrate a cincture apparatus 400 according to another embodiment of the present disclosure. The cincture apparatus 400 includes a tubular member 402 (e.g., a delivery sheath) and a cincture (shown as 404a in FIGS. 4A and 404b in FIG. 4B) disposed on the outer surface of the tubular member 402. The cincture shown in FIGS. 4A and 4B is transitionable from an open configuration 404a to a contracted or closed configuration 404b. The cincture apparatus 400 shown in FIGS. 4A and 4B can be used in conjunction with the tissue eversion apparatuses discussed above to deliver a closure element (such as cincture 404a, 404b) to a portion of everted tissue according to the devices and methods disclosed herein.

The delivery sheath 402 delivers a cincture 404a, which can be held in place on the sheath 402 by a retention structure 406. The retention structure 406 can prevent the cincture 404a from malpositioning and/or from prematurely contracting. In some embodiments, the retention structure 406 can be slidably positioned on the sheath 402, such that the retention structure 406 can be slid distally on the sheath 402 to act as an actuator to slide the cincture 404a off the sheath 402. The cincture 404a, which can be held by the retention structure 406, can be sufficiently rigid to not readily change position and/or can be temporarily held in place by a wax-like or other semi-solid biocompatible material that will give way, allowing the cincture 404a to slide off the sheath 402 and contract.

The cincture 404a can be attached to a retractable suture loop 410, which is contained in a lumen 408, shown in the Figure as a cylindrical structure. The lumen 408 can comprise a narrowed portion 412 that permits the cincture material to pass, but prevents a tightening feature (e.g., a functional slip-knot) from passing. Thus when the suture loop 410 is pulled, the cincture 404a is reduced in diameter and transitioned to the smaller diameter 404b. When the suture loop 410 is pulled in its entirety, the cincture loop 404b completely closes, effecting closure around a portion of everted tissue around an opening (e.g., a puncture wound).

Figure 5A:
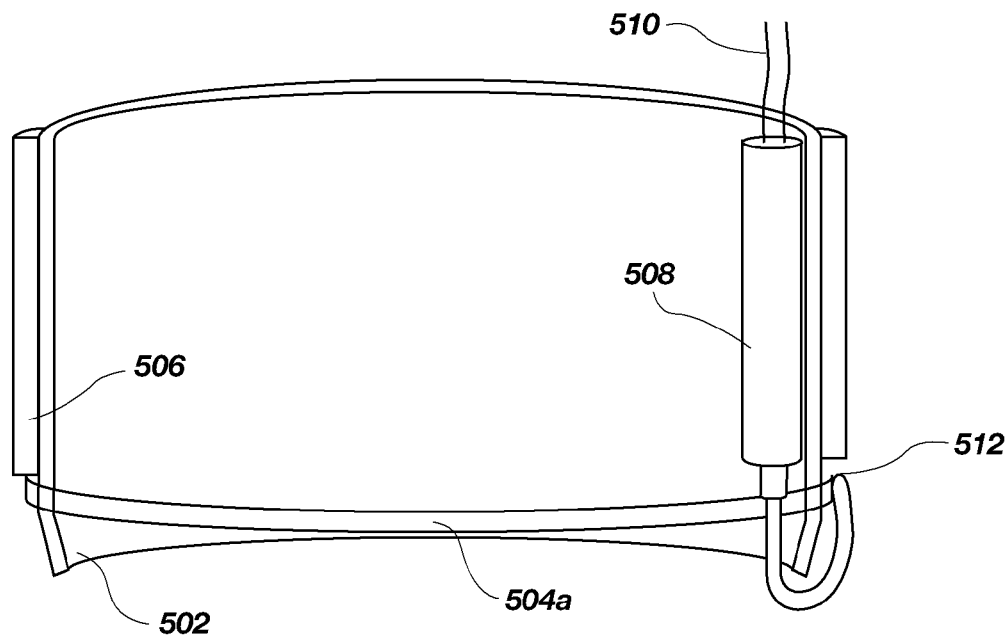
FIGS. 5A and 5B illustrate a tissue cincture apparatus according to one embodiment of the present disclosure.
Figure 5B:
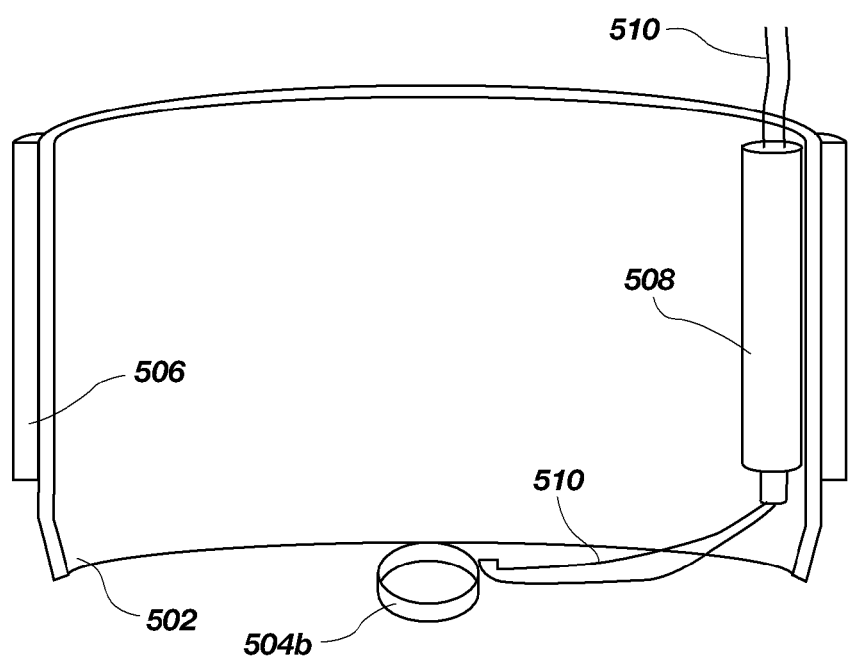

FIGS. 5A and 5B illustrate a cincture apparatus 500 according to yet another embodiment of the present disclosure. The cincture apparatus 500 includes a tubular member 502 (e.g., a delivery sheath) and a cincture (shown as 504a in FIGS. 5A and 504b in FIG. 5B) disposed on the outer surface of the tubular member 502. The cincture shown in FIGS. 5A and 5B, which in this embodiment is formed from a resilient or shape-memory material, can transition from an open configuration 504a to a contracted or closed configuration 504b when the cincture 504a is removed from the tubular member 502. The cincture apparatus 500 shown in FIGS. 5A and 5B can be used in conjunction with the tissue eversion apparatuses discussed above to deliver a closure element (such as cincture 504a, 504b) to a portion of everted tissue according to the devices and methods disclosed herein.

The delivery sheath 502 delivers a cincture 504a, which can be held in place on the sheath 502 by a retention structure 506. The retention structure 506 can prevent the cincture 504a from malpositioning and/or from prematurely contracting. In some embodiments, the retention structure 506 can be slidably positioned on the sheath 502, such that the retention structure 506 can be slid distally on the sheath 502 to act as an actuator to slide the cincture 504a off the sheath 502. The cincture 504a, which can be held by the retention structure 506, can be sufficiently rigid to not readily change position and/or can be temporarily held in place by a wax-like or other semi-solid biocompatible material that will give way, allowing the cincture 504a to slide off the sheath 502 and contract.

The cincture 504a can be attached to a retractable suture loop 510, which is contained in a lumen 508, shown in the Figure as a cylindrical structure. The retractable suture loop 510 can be used to pull the cincture 504a past the end of the sheath 502. If the retention structure 506 is slidably disposed on the sheath 502, or otherwise has the ability to move the cincture past the end of the sheath 502, then the suture loop 510 may not be might not be necessary (although it can still be useful for retrieving misplaced cinctures). When the self contracting cincture 504a is moved past the end of the sheath 502, by action of the suture loop 510 or the retention device 506, the cincture contracts adopting configuration 504b, reducing its radius, effecting closure around a portion of everted tissue around an opening (e.g., a puncture wound).

Figure 6A:
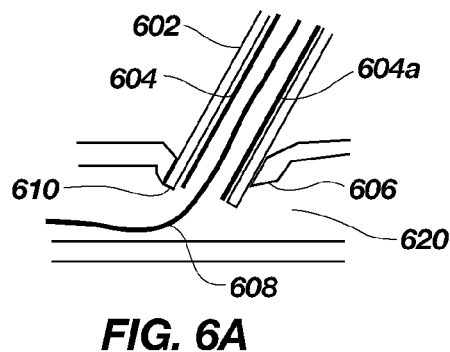
FIGS. 6A-6G schematically illustrate closure of an opening in a body lumen using a tissue eversion apparatus and a tissue cincture apparatus according to one embodiment of the present disclosure.

FIGS. 6A-6G schematically illustrate steps in a method of closing a tissue opening using at least one tubular member, a tissue eversion apparatus, and as cincture closure according to the present disclosure. In FIG. 6A, a sheath 602, for example a sheath like that described in relation to FIG. 1, is guided into an opening in a vessel 620 with the aid of a guidewire 608. The sheath 602 includes elongate tissue engaging members 604a disposed in the lumen of the sheath 620.

Figure 6B:
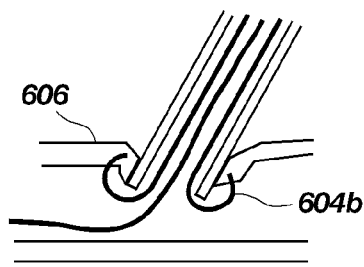
Figure 6C:
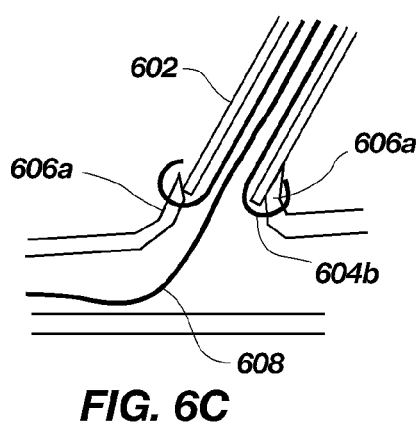

As shown in FIG. 6B, the elongate tissue engaging members 604b are deployed so that they can engage the edges of the opening 606. In a non-limiting example, the tissue engaging members 604b curve back away from sheath 602 when they are deployed so that the tissue engaging members 604b are positioned to engage the tissue around the opening and evert the tissue when the sheath 602 is retracted. As shown in FIG. 6C, once the elongate tissue engaging members 604b are engaged with the tissue edges 606, the sheath 602 can be retracted creating an everted tissue region 606a.

As shown, the elongate tissue engaging members 604b pierce a portion of the everted tissue region 606a. Nonetheless, one will appreciate that the tissue engaging members 604b need not pierce the tissue in order to engage the tissue to form the everted tissue region 606a. For example, any known gripping means such as apposing feet, hooks, teeth, adhesive devices and the like can be used to engage the tissue around the opening to form the everted tissue region.

Figure 6D:
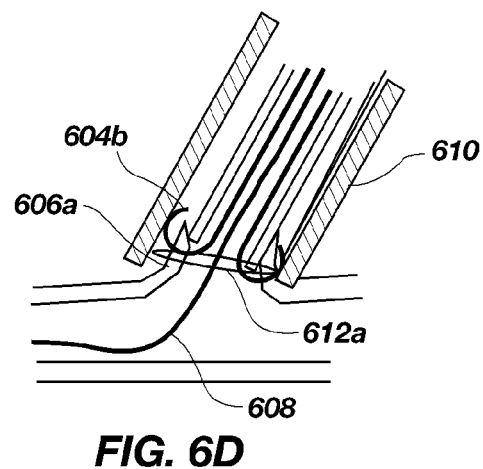
Figure 6E:
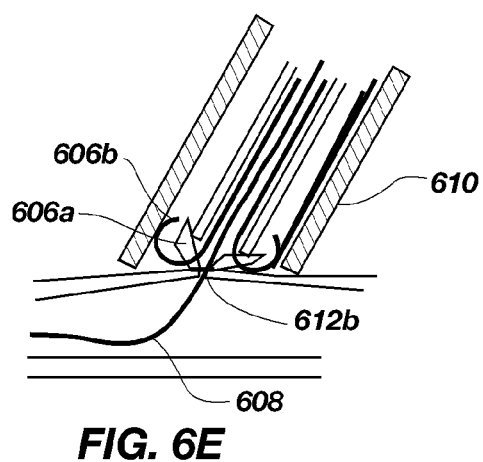

Referring now to FIGS. 6D-6G, a cincture 612a can be advanced from a second sheath 610, and tightened 612b over the everted edges of the opening, as shown in FIG. 6E. As shown in FIGS. 6D-6E, the cincture 612a, 612b is placed around the everted tissue region 606a below the portion of the everted region 606a that is punctured by the tissue engaging members. This ensures that the portions of the vessel that are punctured by the tissue engaging members do not cause additional bleeding after the cincture 612a, 612b is placed. Moreover, placing the cincture 612a, 612b below the portion of the tissue engaged by the tissue engaging members can prevent the tissue engaging members from interfering with complete closure of the opening and/or can facilitate good contact between the vascular epithelial layers to facilitate wound healing.

Figure 6F:
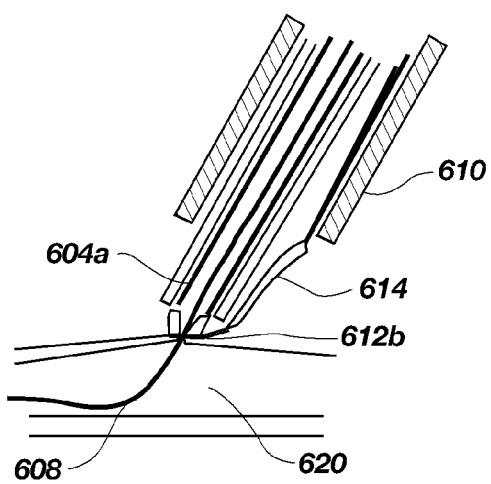
Figure 6G:
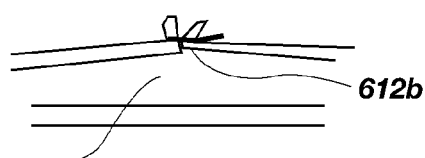

After the cincture 612b is placed, the second sheath 610 can be removed, leaving the opening closed by the cincture 612b, as shown in FIG. 6F. The tissue engaging members 604a can also be retracted into the sheath 602, all as shown in FIG. 6F. The suture loop 614 (if required), tissue engaging members 604a and sheath 602, the second sheath 610, and the guidewire 608 can all be removed, leaving the cincture 612b in place closing the opening in the vessel 620, as shown in FIG. 6G. As will be discussed below in reference to FIGS. 8A-11H, a number of second, redundant closure elements may be applied following placement of the first closure element (e.g., the cincture) in order to provide redundant closure to the opening.

FIGS. 7A-7H illustrate various cincture configurations that can be adapted for use with the devices and methods disclosed herein. Cincture 11, shown in FIG. 7A, illustrates a simple cincture in an open configuration and cincture 12 is the simple cincture of 11 in a closed position. Cinctures 11 and 12 include a slip-knot with only one suture end to be pulled and distal loop for the pulling suture. Cinctures 21 and 22, shown in FIG. 7B, illustrate a cincture configuration with a slip-knot device, with both suture ends to be pulled through the slip-knot device, resulting in a loop of material when the cincture is completely closed. Cinctures 31 and 32, shown in FIG. 7C, illustrate a cincture configuration that includes a loop and the pulling suture is functionally internal to the cincture initially, resulting in very little trailing material when the cincture is completely closed. Cinctures 41 and 42, shown in FIG. 7D, illustrate a cincture configuration that includes dentates on the suture. When cinctures 41 and 42 are closed, the dentates act to lock the suture in the closed position. Cinctures 51 and 52, shown in FIG. 7E, illustrate a cincture configuration that includes multiple strands of material, resulting in a multiple level complex closed cincture. Cinctures 61 and 62, shown in FIG. 7F, illustrate a cincture configuration that includes beads or other geometric structures or grippers that fit together and hold the wound closed when the cincture is closed. Cinctures 71 and 72, shown in FIG. 7G, illustrate a cincture made of memory material, so that when the cincture is released from the delivery sheath it contracts to effect closure of the opening. Cinctures 81 and 82, shown in FIG. 7H, illustrate a cincture made of a rubber-like or memory material, that when pushed off of the delivery sheath, can contract more-or-less uniformly to close the cincture and thereby close the opening or wound.

Additional discussion of cincture apparatuses that can be adapted for use with the devices and methods discussed herein can be found in U.S. patent application Ser. No. 11/508,715, filed 23 Aug. 2006, entitled "VASCULAR CLOSURE METHODS AND APPARATUSES," the entirety of which is incorporated herein by reference.

Figure 8A:
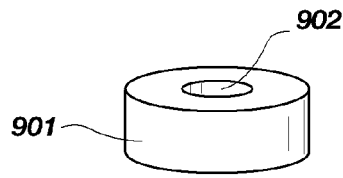
FIGS. 8A-8F illustrate closure of an opening in a body lumen using a redundant closure system according to one embodiment of the present disclosure.
Figure 8B:
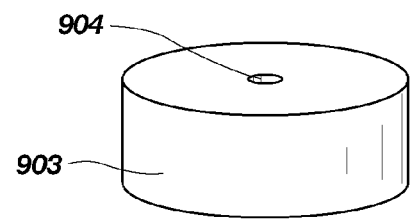

FIGS. 8A-8F illustrate a schematic depiction of a typical embodiment of a hemostatic plug that can be used in combination with a cincture to provide a redundant closure to further reduce the potential failure rate. FIG. 8A demonstrates a typical hemostatic plug 901 made of a biocompatible material preferably shaped as a columnar structure with a cylindrical or toroidal cross section with an internal lumen 902 that permits movement of a grasper device and guidewire. Other cross sectional configurations are possible, with or without a central hole. FIG. 8B demonstrates the hemostatic plug after hydration, where it may assume a larger volume 903 and may decrease the internal diameter of the lumen 904.

Figure 8C:
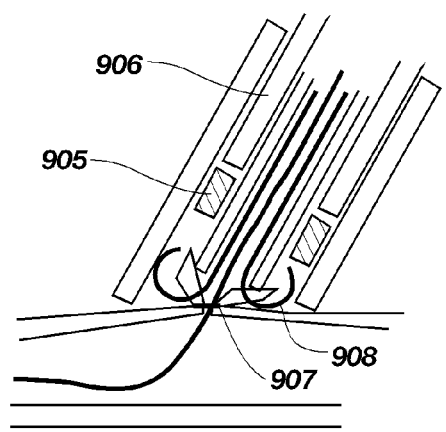
Figure 8D:
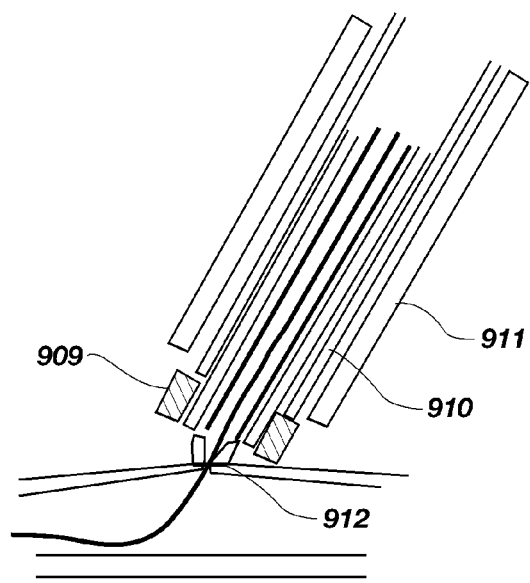
Figure 8E:
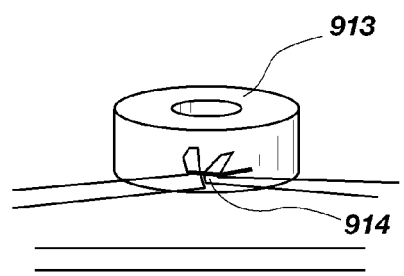
Figure 8F:
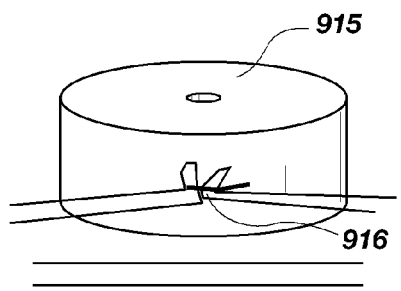

FIG. 8C demonstrates the cincture delivery device with the hemostatic plug 905 and a pushing device 906 which permits expulsion of the hemostatic plug out the suture delivery device onto the closed puncture wound 907 and onto the tines of the tissue engaging members 908. FIG. 8D shows the hemostatic plug 909 being pushed by the expulsion device 910 while the tissue engaging members 908 and cincture delivery device 911 are withdrawn to permit the plug to seat on the puncture wound and the cincture 912. FIG. 8E shows the expulsed hemostatic plug 913 seated directly over the cinctured puncture wound 914. FIG. 8F shows the expulsed hemostatic plug 915 after it has assumed its fully hydrated shape applying pressure to and/or further sealing the cinctured puncture 916. It is to be understood the cincture could be temporary to achieve immediate hemostasis while the plug is adhering to local tissues, and then the cincture could be removed using a number of methods leaving the plug as the primary hemostatic instrument.

Figure 9A:
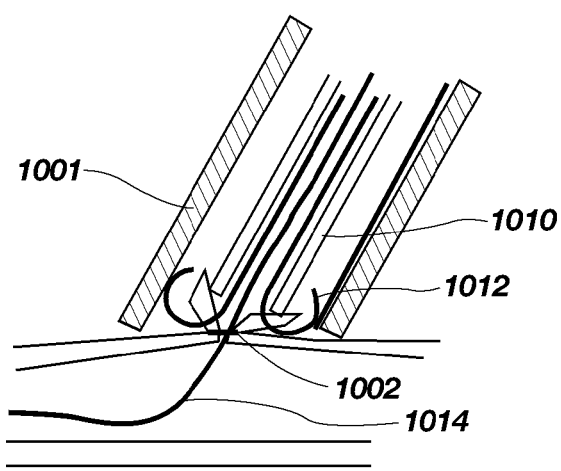
FIGS. 9A-9E illustrate closure of an opening in a body lumen using a redundant closure system according to one embodiment of the present disclosure.
Figure 9B:
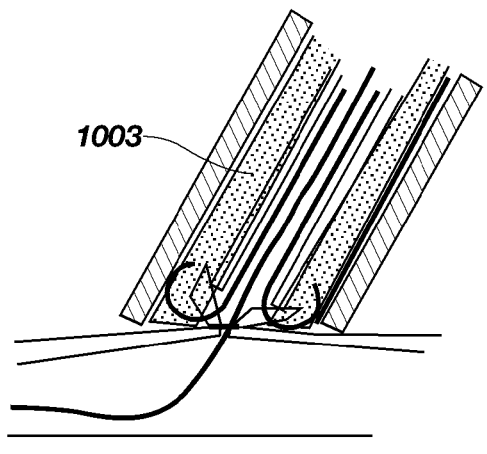
Figure 9C:
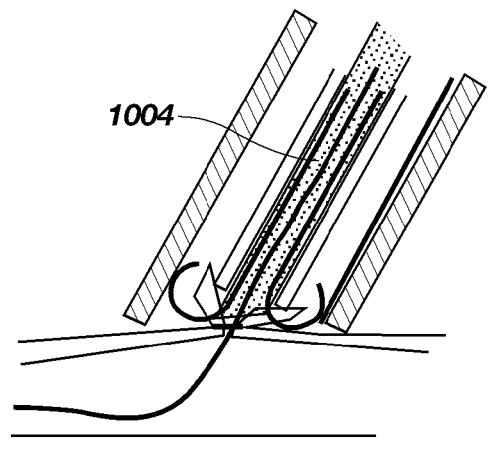
Figure 9D:
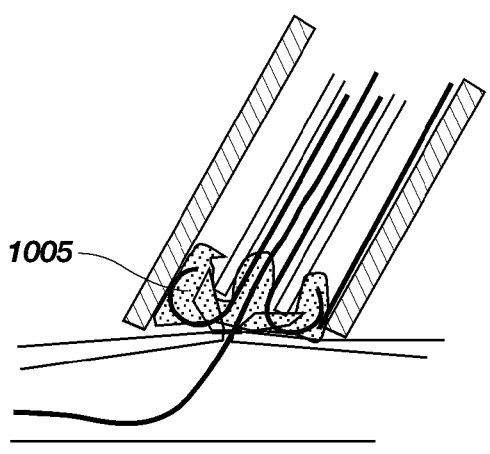
Figure 9E:
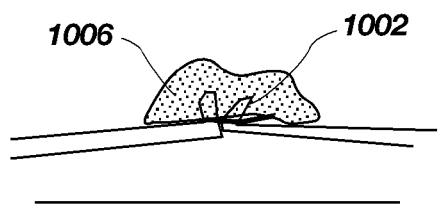

FIG. 9A-9F illustrate a schematic depiction of a typical embodiment of a cincture closure device combined with a biocompatible injectable adhesive or occluding material to provide redundant wound closure. The biocompatible injectable adhesive or occluding material may be bioabsorbable and/or bioresorbable or not. FIG. 9A depicts the cincture delivery device 1001 with a cincture seated 1002 on the puncture wound and a tissue eversion apparatus 1010 with tissue engaging members 1012 engaged with the everted tissue. FIG. 9B demonstrates injectable or extrudable adhesive or occluding material 1003 being injected through the cincture delivery device 1001 and around the tissue eversion apparatus 1010. In the alternative, FIG. 9C demonstrates an injectable or extrudable adhesive or occluding material 1004 being injected through the lumen of the tissue eversion apparatus 1010. FIG. 9D depicts the injected adhesive or occlusive material 1005 surrounding the cincture 1002. FIG. 9E depicts the injected adhesive or occlusive material 1006 surrounding, sealing, and/or further binding the puncture wound and cincture 1002. Note that the cincture 1002 can prevent the adhesive or occlusive material 1006 from entering the blood vessel.

Figure 10A:
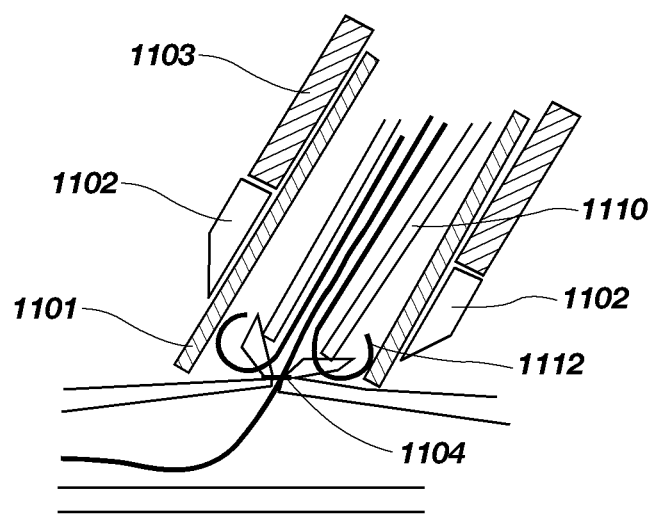
FIGS. 10A-10C illustrate closure of an opening in a body lumen using a redundant closure system according to one embodiment of the present disclosure.
Figure 10B:
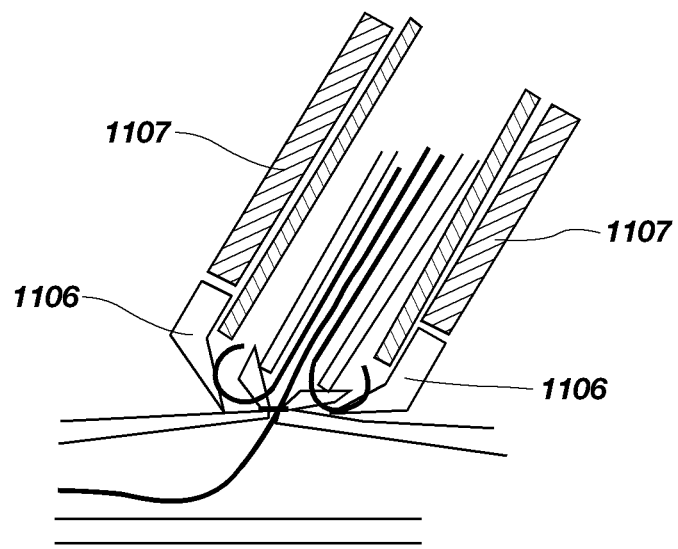
Figure 10C:
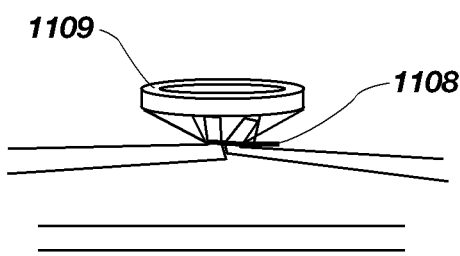

FIGS. 10A-10C illustrate a schematic depiction of the application of an extramural clip over a cincture device in order to provide redundant closure. FIG. 10A illustrates a tissue eversion apparatus 1110 with tissue engagement members 1112 engaged with a portion of everted tissue, a cincture delivery device 1101, a clip 1102 riding on the cincture delivery device 1101, a device 1103 that pushes the clip 1102, a cincture 1108 over the puncture wound 1104. FIG. 10B represents the clip 1106 being pushed off the cincture delivery device 1101 by the pushers 1107. FIG. 20C shows a representation of the clip 1109 residing on the closed puncture 1104, providing redundancy for the cincture closure 1108. It is to be understood the cincture 1108 could be temporary to achieve immediate hemostasis.

The clip 1102 shown in FIGS. 10A-10C can include a base member shaped to allow passage of the clip over the delivery sheath 1102, and a plurality of grasping members that are configured to engage with the everted tissue region (e.g., 606a in FIG. 6A). The base member can be shaped as a ring or a complete circular or cylindrical band, or the base member can be a discontinuous circle to better accommodate the delivery sheath 1102. The base member can also include shape memory materials to better accommodate the delivery sheath 1102 and to assume a lower profile when delivered (e.g., clip 1109). The clip 1102 can include as few as two grasping members and as many as are practical within applicable design considerations. The grasping members can include textured portions or attachments, mating portions with apposing feet, penetrating devices, hooks, teeth, or other adaptations to allow firm grip of the everted tissue region proximal to the tissue cincture.

Figure 11A:
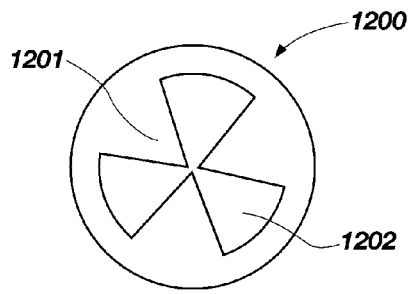
FIGS. 11A-11H illustrate closure of an opening in a body lumen using a redundant closure system according to one embodiment of the present disclosure.
Figure 11B:
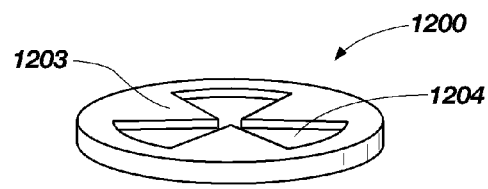
Figure 11C:
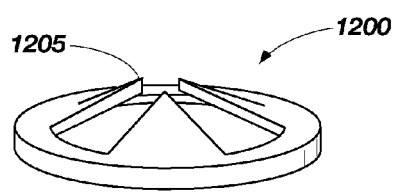

FIGS. 11A-11H illustrate a schematic depiction of an alternate design of an extramural clip 1200 that can be used to provide redundant closure over a cincture. FIG. 11A represents a typical wafer clip 1200 or collar consisting of a disk-like structure with inwardly protruding members 1201 having sharpened or compressive ends, and a space 1202 between the members 1201. FIG. 11B is an oblique of the typical wafer clip 1200 demonstrating the members 1203 and intermember spaces 1204. FIG. 11C represents an important property of the hemostatic adherent wafer clip 1200, that the members 1201, although sharp and rigid or semi-rigid, can be displaced 1205 under force, but are resilient and return to the planar low energy state as shown in FIG. 11B.

Figure 11D:
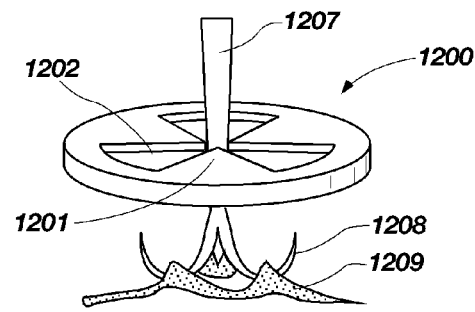
Figure 11E:
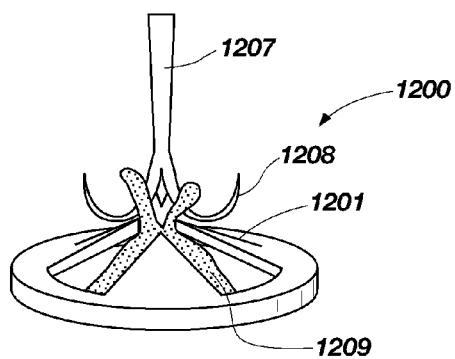

FIG. 11D demonstrates the interaction of the hemostatic adherent wafer clip 1200 and its intermember spaces 1202 with a tissue eversion apparatus 1207, the tissue engaging members 1208 have engaged the wound edges 1209 of the puncture. In FIG. 11E, tissue engaging members 1208 have been pulled through the intermember spaces 1202 of the wafer clip 1200, pulling the wound edges 1211 through the hemostatic clip 1200, and members 1208 engaging and holding the puncture wound edges in opposition and closing the wound.

Figure 11F:
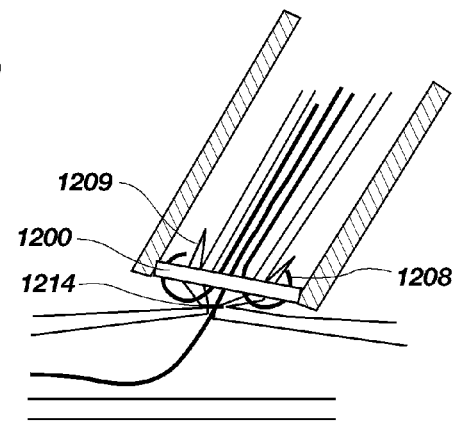
Figure 11G:
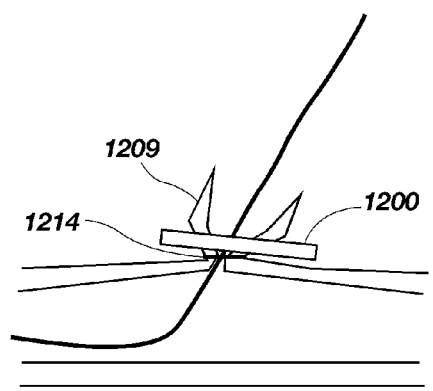
Figure 11H:
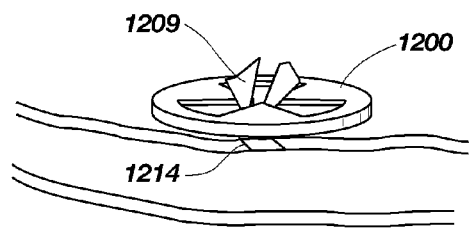

FIG. 11F shows a hemostatic clip 1200 engaging puncture wound tissues after a cincture 1214 has been placed. FIG. 11G shows the hemostatic wafer clip 1200 providing redundant closure in addition to the cincture 1214. FIG. 11H shows the hemostatic wafer clip members 1200 seated on the wound edges 1218 providing redundant closure to the cincture 1214.

Additional discussion of clip apparatuses that can be adapted for use with the devices and methods discussed herein can be found in U.S. patent application Ser. No. 11/508,656, filed 23 Aug. 2006, entitled "VASCULAR CLOSURE METHODS AND APPARATUSES," the entirety of which is incorporated herein by reference.

Additional examples of second, redundant closure elements that can be applied to or around the wound after placing the first closure element can include, but are not limited to, RF energy, thermal energy, electrical induction, infrared light, ultrasonic vibration, microwave or laser irradiation, sutures, and combinations thereof. For example, heat (i.e., thermal energy) can be applied to the wound region after applying the first closure element to cauterize the wound and provide redundant closure.

The embodiments shown in the Figures presented herein show the tissue eversion apparatus and the first and second closure elements being delivered by separate elongate members (i.e., sheaths). One will appreciate, however, that the figures are presented for illustrative purposes and that the tissue eversion apparatus and the first and second closure elements can be delivered by a single elongate member.

Examples of knots that can be suitable for use with the present disclosure include, but are not limited to, the overhand knot or half knot, the double overhand knot, the multi-fold-overhand-knot, the Flemish eight, hitches (single simple, half, clove, two half, buntline, rolling Magnus, midshipman's tautline, adjustable jamming, cow, reversed half, lobster buoy), single loops (bowline, Dutch marine bowline, cowboy bowline, double figure-of-eight loop, Flemish eight, bowstring knot, tucked double overhand, butterfly loop, lineman's loop, artillery loop, pendant hitch), clove hitch, reef knot, square knot, noose (simple noose, strangle-snare, scaffold knot, gallows knot, hangman's knot, reverse eight-noose), monkey fist, the dolly, fisherman's bend, surgeon's knot, sheet bend knot, timber hitch, fisherman's knot, reef knot, square knot, DuraKnot, sliding knots, simple sliding knot, Nicky's knot, Roeder's knot, Seoul Medical Centre knot, Smith & Nephew's knot, Tennesee's knot, purse string, surgical knot with extra loop, other knots and/or cincture devices or combinations thereof could also be used and are anticipated. Endoscopic knot tying devices and suture cutting devices can also be used to create the cincture for this device and are also anticipated.

Examples of suture material at can be suitable for use with the present disclosure include, but are not limited to, absorbable, non-absorbable, braided, monofilament, pseudo-monofilament, multifilament, barbed, smooth, directional, and bidirectional. The suture material can be composed of but not limited to polyglycolic acid, polydioxanon, polylactate, polycaprone, silk, linen, cotton, treated and non-treated collagen, "catgut", chromic, Vicryl, Monocyrl, PDS, polyester, poypropylene, polyamide, stainless steel, and others. The cincture device can be made from other suitable materials, including typical suture materials, flexible polymeric materials with elastomeric properties including polyurethane, polyethylene, polyestenurethane, polyimide, olyethreimide, polycarbonate, polysiloxane, polyvinyls, hydroxyethylmethacrylate, related polymers, co-polymers of these or other polymers, or drug-embedded or drug-eluting polymers to prevent coagulation or intimal hyperplasia (such as Taxol), also which can be made radiopaque by markers and addition of appropriate radiopaque materials.

The tines or gripping portion of a the tissue engaging members or components of the sheath or cincture device can be made from any number of suitable materials, including radiopaque materials and materials coated to be made radiopaque, including bioabsorbable polymers or compounds, non-absorbable alloys and compounds including stainless steel, MP35, Nitinol, Nickel-Titanium alloy, Kevlar, nylon polyester acrylic, gold, platinum, tantalum, niobium, molybdenum, rhodium, palladium silver, hafnium, tungsten, iridium. Materials with memory can be useful to allow tines to spontaneously open after extended from the sheath. These can be made in the form of wires, fibers, filaments, small beams, and other extruded, woven, or formed shapes. Piano wire, super elastic memory wire, chromium allows, alloys of titanium and nickel, and other elastic memory materials previously mentioned as well as others can be used as well.

The sealant plug, injected sealant, and injected occlusive material can be composed of an appropriate biocompatible materials including but not limited to fibrin and cross-linked fibrin autologous blood clot formed by blood mixed with topical thrombin, the above clot treated with epsilon-aminocaproic acid providing a more stable clot and delaying lysis; Gelfoam, Ivalon, Oxycel and other particulate materials, biocompatible polymer including an alginate, chitosan and poly-L-amino acid, sodium alginate, potassium alginate, strontium alginate, barium alginate, magnesium alginate or any other alginate or a mixture thereof; poly-L-lysine, poly-L-arginine, poly-L-glutamic acid, poly-L-histidine, poly-a-D-glutamic acid or a mixture thereof; platelet-rich plasma and a biocompatible polymer; mixture of fibrin and fibrinogen; fibrin microbeads, collagen, cross-linked collagen and other collagen-derivatives, polysaccharides, cellulosics, polymers (natural and synthetic), inorganic oxides, ceramics, zeolites, glasses, metals, and composites; dextran beads;

microporous polysaccharide beads; tackified natural rubbers; synthetic rubbers such as butyl rubber; and tackified linear, radial, star, and branched and tapered styrene block copolymers, such as styrene-butadiene, styrene-ethylene/butylene and styrene-isoprene; polyurethanes; polyvinyl ethers; acrylics, especially those having long chain alkyl groups; poly-a-olefins; and silicones; a platelet glue (platelets-fibrinogen-fibrinogen activator) wound sealant; pressure glues, polymer glues, polyglycolic acid, polydioxanon, polylactate, polycaprone; flexible polymeric materials with elastomeric properties including polyurethane, polyethylene, polyestenurethane, polyimide, olyethreimide, polycarbonate, polysiloxane, polyvinyls, hydroxyethylmethacrylate, related polymers, co-polymers of these or other polymers, or drug-embedded or drug-eluting polymers to prevent coagulation or intimal hyperplasia (such as Taxol), also which can be made radiopaque by markers and addition of appropriate radiopaque materials.

The extraluminal clip and/or hemostatic wafer clip could be constructed of any of the above absorbable or non-absorbable materials but also any number of suitable materials, including radiopaque materials and materials coated to be made radiopaque, including bioabsorbable polymers or compounds, non-absorbable alloys and compounds including stainless steel, MP35, Nitinol, Nickel-Titanium alloy, Kevlar, nylon polyester acrylic, gold, platinum, tantalum, niobium, molybdenum, rhodium, palladium silver, hafnium, tungsten, iridium.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A closure device for closing an opening in a tissue, the closure device comprising:
    a tubular member having a proximal end and a distal end region, an exterior surface, and a lumen extending along an entire length of the tubular member;
    a tissue eversion apparatus configured to form an everted tissue region, the tissue eversion apparatus having a plurality of elongate tissue engaging members disposed within the lumen of the tubular member and deployable therefrom, in a deployed position the elongate tissue engaging members having ends thereof configured to engage the tissue surrounding the opening, and in the deployed position the elongate tissue engaging members curve away from center axes of each of the elongate tissue engaging members thereof in a manner that the ends thereof face away from each other, for approximating and everting edges of the tissue engaged by the elongate tissue engaging members;
    a first closure element operatively coupled to the tubular member and deliverable therefrom for closing the opening, the first closure element being held in place in the lumen of the tubular member by a retention structure; the first closure element being a cincture element having a first size and a second size that is smaller than the first size; the first size being configured to surround a portion of the everted tissue region around the opening; and the second size being configured to capture the portion of the everted tissue region and close the opening when the cincture element is transitioned from the first size towards the second size.

2. The closure device of claim 1, the first closure element being disposed within the lumen of the tubular member and being deployable therefrom.

3. The closure device of claim 1, the elongate tissue engaging members of the tissue eversion apparatus having a first configuration substantially parallel to an axis of the tubular member when disposed within the tubular member, and having a second configuration curving away from the axis of the tubular member when the elongate tissue engaging members are projected out of the lumen.

4. The closure device of claim 3, the tissue eversion apparatus being moveable relative to the tubular member along the axis of the tubular member,
    motion of the tissue eversion apparatus along the axis past the end of the distal end of the tubular member allowing the plurality of elongate tissue engaging members to attain the second configuration, and
    retraction of the tissue eversion apparatus into the distal end of the tubular member allowing the plurality of elongate tissue engaging members to attain the first configuration.

5. The closure device of claim 1, the elongate tissue engaging members having sharpened ends configured to penetrate a portion of the everted tissue region.

6. The tissue closure device of claim 1, further comprising a closure actuator coupled to the first closure element, the closure actuator adapted to distally advance the first closure element from a region proximal to the everted tissue region to a region surrounding the everted tissue region, and the closure actuator being further adapted to transition the first closure element from the first size to the second size.

7. The tissue closure device of claim 1, the cincture element being a loop of suture having at least one pre-tied slip-knot.

8. The tissue closure device of claim 1, the first closure element being constructed of a bioabsorbable material.

9. The closure device of claim 1, the retention structure substantially preventing the cincture element from malpositioning or prematurely contracting.

10. The closure device of claim 1, the retention structure comprising a semi-solid biocompatible material.

11. The closure device of claim 10, the semi-solid biocompatible material comprising a wax-like material.

12. A closure device for closing an opening in a tissue, the closure device comprising:
    a first tubular member having a proximal end and a distal end region, an exterior surface, and a lumen extending along an entire length of the tubular member;
    a tissue eversion apparatus configured to form an everted tissue region, the tissue eversion apparatus having a plurality of elongate tissue engaging members disposed within the lumen of the first tubular member and deployable therefrom, in a deployed position the elongate tissue engaging members having ends thereof configured to engage the tissue surrounding the opening, and in the deployed position the elongate tissue engaging members curve away from center axes of each of the elongate tissue engaging members thereof in a manner that the ends thereof face away from each other, for approximating and everting edges of the tissue engaged by the elongate tissue engaging members;
    a second tubular member having a proximal end and a distal end region, an exterior surface, and a lumen extending along an entire length of the tubular member;
    a first closure element operatively coupled to the second tubular member and deliverable therefrom for closing the opening, the first closure element comprising a cincture element held in place in the lumen of the second tubular member by a retention structure, the retention structure substantially preventing the cincture element from malpositioning or prematurely contracting.

13. The closure device of claim 12, the second tubular member being slidable over the first tubular member.

14. The closure device of claim 12, the first closure element being disposed within the lumen of the second tubular member and being deployable therefrom.

15. The closure device of claim 12, the elongate tissue engaging members having sharpened ends configured to penetrate an interior surface of the edges of the tissue to be closed to form the everted tissue region.

16. The tissue closure device of claim 12, the first closure element being a cincture element having a first size and a second size that is smaller than the first size;
the first size being configured to surround a portion of the everted tissue region around the opening; and
the second size being configured to capture the portion of the everted tissue region and close the opening when the cincture element is transitioned from the first size towards the second size.

17. The tissue closure device of claim 16, further comprising a closure actuator coupled to the first closure element, the closure actuator adapted to distally advance the first closure element from a region proximal to the everted tissue region to a region surrounding the everted tissue region, and the closure actuator being further adapted to transition the first closure element from the first size to the second size.

18. The tissue closure device of claim 16, the cincture element being a loop of suture having at least one pre-tied slip-knot.

19. The tissue closure device of claim 18, the loop of suture including at least one dentate configured to maintain the cincture element in a closed position.

20. The tissue closure device of claim 16, the cincture element being formed from a shape memory material having an expanded delivery configuration and a contracted deployed configuration that resiliently closes the opening when the first closure element is deployed around the everted tissue region.

21. The tissue closure device of claim 12, further comprising a second closure element being selected from a group consisting of sealant plugs, adhesive glues, occlusive substances, extraluminal clips, RF energy, thermal energy, electrical induction, infrared light, ultrasonic vibration, microwave or laser irradiation, sutures, and combinations thereof.

22. The tissue closure device of claim 12, the first closure element being constructed of a bioabsorbable material.

23. The closure device of claim 12, the retention structure comprising a semi-solid biocompatible material.

24. The closure device of claim 23, the semi-solid biocompatible material comprising a wax-like material.

* * * * *